(12) United States Patent
Bigg et al.

(10) Patent No.: US 7,186,752 B2
(45) Date of Patent: Mar. 6, 2007

(54) DERIVATIVES OF N-(IMINOMETHYL)AMINES, THEIR PREPARATION, THEIR USE AS MEDICAMENTS AND THE PHARMACEUTICAL COMPOSITIONS CONTAINING THEM

(75) Inventors: Dennis Bigg, Gif-sur-Yvette (FR); Pierre-Etienne Chabrier de Lassauniere, Paris (FR); Serge Auvin, Mauchamps (FR); Jeremiah Harnett, Gif-sur-Yvette (FR); Gérard Ulibarri, Burres-sur-Yvette (FR)

(73) Assignee: SCRAS (FR)

( * ) Notice: Subject to any disclaimer, the term of this patent is extended or adjusted under 35 U.S.C. 154(b) by 127 days.

(21) Appl. No.: 11/114,803

(22) Filed: Apr. 26, 2005

(65) Prior Publication Data

US 2005/0197329 A1 Sep. 8, 2005

Related U.S. Application Data

(62) Division of application No. 10/895,578, filed on Jul. 21, 2004, now abandoned, which is a division of application No. 10/612,646, filed on Jul. 1, 2003, now Pat. No. 6,809,090, which is a division of application No. 10/255,849, filed on Sep. 26, 2002, now Pat. No. 6,620,840, which is a division of application No. 09/787,466, filed as application No. PCT/FR99/02251 on Sep. 22, 1999, now Pat. No. 6,482,822.

(30) Foreign Application Priority Data

Sep. 23, 1998 (FR) .................................. 98 11867

(51) Int. Cl.
*C07D 401/12* (2006.01)
*C07D 403/12* (2006.01)
*C07D 307/91* (2006.01)
*C07D 31/352* (2006.01)

(52) U.S. Cl. .................. 514/468; 514/254.11; 514/218; 514/326; 514/365; 514/422; 514/444; 544/375; 546/196; 549/60; 549/460; 549/461; 540/575

(58) Field of Classification Search ................ 549/460, 549/461, 60; 514/468, 254.11, 218, 326, 514/365, 422, 444; 540/575; 544/375; 546/196; 548/146, 525
See application file for complete search history.

(56) References Cited

U.S. PATENT DOCUMENTS 6,172,104 B1 * 1/2001 Tidwell et al. .............. 514/443

* cited by examiner

*Primary Examiner*—Kahsay Habte
(74) *Attorney, Agent, or Firm*—Charles A. Muserlian

(57) ABSTRACT

N-(imino)amines and their preparation and their use as NO synthase inhibitors and selective or non-selective traps for a reactive oxygen species.

7 Claims, No Drawings

DERIVATIVES OF N-(IMINOMETHYL)AMINES, THEIR PREPARATION, THEIR USE AS MEDICAMENTS AND THE PHARMACEUTICAL COMPOSITIONS CONTAINING THEM

This application is a division of U.S. patent application Ser. No. 10/895,578 filed Jul. 21, 2004, now abandoned, which is a division of U.S. patent application Ser. No. 10/612,646 filed Jul. 1, 2003, now U.S. Pat. Ser. No. 6,809,090, which is a division of U.S. patent application Ser. No. 10/255,849, now U.S. Pat. Ser. No. 6,620,840, which is a division of U.S. patent application Ser. No. 09/787,466 filed Mar. 16, 2001, now U.S. Pat. Ser. No. 6,482,822, which is a 371 of PCT/FR99102251 filed Sep. 22, 1999.

A subject of the present invention is new derivatives of N-(iminomethyl)amines comprising the aminodiphenylamine, oxodiphenylamine, carbazole, phenazine, phenothiazine, phenoxazine or oxodiphenyl unit in their skeleton. These derivatives have an inhibitory activity on NO-synthase enzymes producing nitrogen monoxide NO and/or an activity which traps the reactive oxygen species (ROS). The invention relates to the derivatives corresponding to general formula (I) defined below, their preparation methods, the pharmaceutical preparations containing them and their use for therapeutic purposes, in particular their use as NO-synthase inhibitors and selective or non selective traps for reactive oxygen species.

Given the potential role of NO and the ROS's in physiopathology, the new derivatives described corresponding to general formula (I) may produce beneficial or favourable effects in the treatment of pathologies where these chemical species are involved. In particular:

Proliferative and inflammatory diseases such as for example atherosclerosis, pulmonary hypertension, respiratory distress, glomerulonephritis, portal hypertension, psoriasis, arthrosis and rheumatoid arthritis, fibroses, angiogenisis, amyloidoses, inflammations of the gastro-intestinal system (ulcerous or non-ulcerous colitis, Crohn's disease), diarrhoea.

Diseases affecting the pulmonary system and airways (asthma, sinusitis, rhinitis).

Cardio-vascular and cerebro-vascular disorders including for example, migraine, arterial hypertension, septic shock, ischemic or hemorragic, cardiac or cerebral infarctions, ischemias and thromboses.

Disorders of the central or peripheral nervous system such as for example neurodegenerative diseases where there can in particular be mentioned cerebral infarctions, sub-arachnoid haemorrhaging, ageing, senile dementias including Alzheimer's disease, Huntington's chorea, Parkinson's disease, Creutzfeld Jacob disease and prion diseases, amyotrophic lateral sclerosis; ocular neuropathies such as glaucoma but also pain, cerebral and bone marrow traumas, addiction to opiates, alcohol and addictive substances, cognitive disorders, encephalopathies, encephalopathies of viral or toxic origin.

Disorders of the skeletal muscle and neuromuscular joints (myopathy, myosis) as well as cutaneous diseases.

Cataracts.

Organ transplants.

Auto-immune and viral diseases such as for example lupus, AIDS, parasitic and viral infections, diabetes and its complications, multiple sclerosis.

Cancer.

Neurological diseases associated with intoxications (Cadmium poisoning, inhalation of n-hexane, pesticides, herbicides), associated with treatments (radiotherapy) or disorders of genetic origin (Wilson's disease).

all the pathologies characterized by an excessive production or dysfunction of NO and/or ROS's.

In all these pathologies, there is experimental evidence demonstrating the involvement of NO or ROS's (*J. Med. Chem.* (1995) 38, 4343–4362; *Free Radic. Biol. Med.* (1996) 20, 675–705; *The Neuroscientist* (1997) 3, 327–333).

Moreover, in earlier patents, the inventors have already described NO Synthase inhibitors and their use (U.S. Pat. Nos. 5,081,148; 5,360,925) and more recently the combination of these inhibitors with products having antioxidant or antiradicular properties (Patent Application PCT WO/09653). They have also described in not yet published Applications other derivatives of amidines or, more recently, derivatives of aminopyridines. These derivatives of amidines or aminopyridines have the characteristic of being both NO Synthase inhibitors and ROS inhibitors.

A subject of the present invention is new derivatives of amidines, their preparation and their use in therapeutics.

The compounds of the invention correspond to general formula (I):

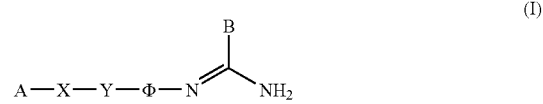

in which

Φ represents a bond or a phenylene radical which can include, in addition to the two chains already represented in general formula (I), up to two substituents chosen from a hydrogen atom, a halogen, an OH group, and a linear or branched alkyl or alkoxy radical having 1 to 6 carbon atoms;

A represents a

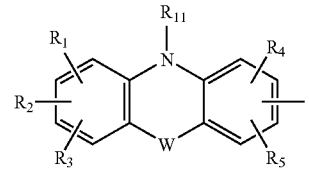

radical in which $R_1$, $R_2$, $R_3$, $R_4$, $R_5$ represent, independently, a hydrogen atom, a halogen, the OH group, a linear or branched alkyl or alkoxy radical having 1 to 6 carbon atoms, or a cyano, nitro or $NR_6R_7$ radical, $R_6$ and $R_7$ representing, independently, a hydrogen atom, the OH group, a linear or branched alkyl or alkoxy radical having 1 to 6 carbon atoms, or also a —$COR_8$ group, $R_8$ representing a hydrogen atom, the OH group, a linear or branched alkyl or alkoxy radical having 1 to 6 carbon atoms, or $NR_9R_{10}$, $R_9$ and $R_{10}$ representing, independently, a hydrogen atom, the OH group or a linear or branched alkyl radical having 1 to 6 carbon atoms, $R_{11}$ representing a hydrogen atom, the OH group, a linear or branched alkyl or alkoxy radical having 1 to 6 carbon atoms, or a —$COR_{12}$ radical, and $R_{12}$ representing a hydrogen atom, the OH group, a linear or branched alkyl radical having 1 to 6 carbon atoms, or a

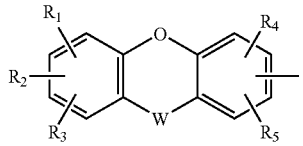

radical in which $R_1$, $R_2$, $R_3$, $R_4$, $R_5$ represent, independently, a hydrogen atom, a halogen, the OH group, a linear or branched alkyl or alkoxy radical having 1 to 6 carbon atoms, or a cyano, nitro or $NR_6R_7$ radical, $R_6$ and $R_7$ representing, independently, a hydrogen atom, the OH group, a linear or branched alkyl or alkoxy radical having 1 to 6 carbon atoms, or also a —$COR_8$ group, $R_8$ representing a hydrogen atom, the OH group, a linear or branched alkyl or alkoxy radical having 1 to 6 carbon atoms, or $NR_9R_{10}$, $R_9$ and $R_{10}$ representing, independently, a hydrogen atom, the OH group or a linear or branched alkyl radical having 1 to 6 carbon atoms, B represents —$CH_2$—$NO_2$, a linear or branched alkyl radical having 1 to 6 carbon atoms, carbocyclic or heterocyclic aryl with 5 or 6 members containing 1 to 4 heteroatoms chosen from O, S, N and in particular the thiophene, furan, pyrrole or thiazole radical, the aryl radical being optionally substituted by one or more groups chosen from linear or branched alkyl, alkenyl or alkoxy radicals having 1 to 6 carbon atoms, or B represents an $NR_{13}R_{14}$ radical, in which $R_{13}$ and $R_{14}$ representing, independently, a hydrogen atom or a linear or branched alkyl radical having 1 to 6 carbon atoms or a cyano or nitro radical, or $R_{13}$ and $R_{14}$ form with the nitrogen atom a non aromatic heterocycle with five to six members, the elements of the chain being chosen from a group composed of —$CH_2$—, —NH—, —O— or —S—;

W does not exist, or represents a bond, or O, S or $NR_{15}$, in which $R_{15}$ represents a hydrogen atom or a linear or branched alkyl radical having 1 to 6 carbon atoms;

X represents a bond or a $(CH_2)_k$—$NR_{16}$—, —O—, —S—, —CO—, —$NR_{16}$—CO—, —CO—$NR_{16}$—, —O—CO—, —CO—O—, —$NR_{16}$—CO—O—, —$NR_{16}$—CO—$NR_{17}$— radical, k representing 0 or 1;

Y represents a bond or a radical chosen from the $-(CH_2)_m-$, $-(CH_2)_m-O-(CH_2)_n-$, $-(CH_2)_m-S-(CH_2)_n-$, $-(CH_2)_m-NR_{18}-(CH_2)_n-$, $-(CH_2)_m-NR_{18}-CO-(CH_2)_n-$, $-(CH_2)_m-CO-NR_{18}-(CH_2)_n-$, $-(CH_2)_m-Q-(CH_2)_n-$ radicals, Q representing piperazine, homopiperazine, 2-methylpiperazine, 2,5-dimethylpiperazine, 4-oxypiperidine or 4-aminopiperidine radicals, m and n being integers from 0 to 6;

$R_{16}$, $R_{17}$ and $R_{18}$ represent, independently, a hydrogen atom or a linear or branched alkyl radical having 1 to 6 carbon atoms;

or are salts of the products mentioned previously.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By linear or branched alkoxy having 1 to 6 carbon atoms, is meant the alkyl radical of which has the meaning indicated previously. Finally, by halogen, is meant fluorine, chlorine, bromine or iodine atoms.

Preferably, the compounds according to the invention are the compounds of general formula (I) such that:

A represents a

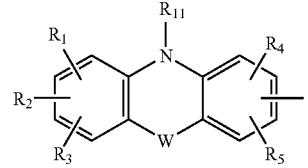

radical in which $R_1$, $R_2$, $R_3$, $R_4$, $R_5$ represent, independently, a hydrogen atom, the OH group or a linear or branched alkyl or alkoxy radical having 1 to 6 carbon atoms, $R_{11}$ representing a hydrogen atom or a linear or branched alkyl radical having 1 to 6 carbon atoms, or a

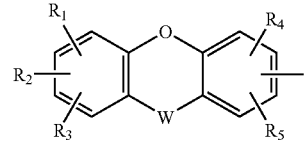

radical in which $R_1$, $R_2$, $R_3$, $R_4$, $R_5$ represent, independently, a hydrogen atom, the OH group or a linear or branched alkyl or alkoxy radical having 1 to 6 carbon atoms;

B represents a carbocyclic or heterocyclic aryl radical with 5 or 6 members containing 1 to 4 heteroatoms chosen from O, S, N and in particular the thiophene, furan, pyrrole or thiazole radicals, the aryl radical being optionally substituted by one or more groups chosen from linear or branched alkyl, alkenyl or alkoxy radicals having 1 to 6 carbon atoms;

W does not exist, or represents a bond, S or $NR_{15}$, in which $R_{15}$ represents a hydrogen atom or a linear or branched alkyl radical having 1 to 6 carbon atoms;

X represents a bond or a —$(CH_2)_k$—$NR_{16}$—, —O—, —S—, —CO—, —$NR_{16}$—CO—, —CO—$NR_{16}$—, —O—CO—, —CO—O—, —$NR_{16}$—CO—O—, —$NR_{16}$—CO—$NR_{17}$—radical k representing 0 or 1;

Y represents a bond or a radical chosen from the $-(CH_2)_m-$, $-(CH_2)_m-O-(CH_2)_n-$, $-(CH_2)_m-S-(CH_2)_n-$, $-(CH_2)_m-NR_{18}-(CH_2)_n-$, $-(CH_2)_m-NR_{18}-CO-(CH_2)_n-$, $-(CH_2)_m-CO-NR_{18}-(CH_2)_n-$, $-(CH_2)_m-Q-(CH_2)_n-$ radicals, Q representing piperazine, homopiperazine, 2-methylpiperazine, 2,5-dimethylpiperazine, 4-oxypiperidine or 4-aminopiperidine, m and n being integers from 0 to 6;

or are salts of the products mentioned previously.

More preferably, the compounds according to the invention are compounds of general formula (I) such that:

A represents a

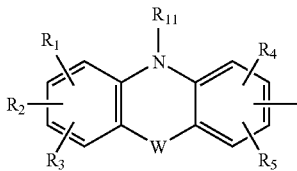

radical in which $R_1$, $R_2$, $R_3$, $R_4$ and $R_5$ represent, independently, a hydrogen atom, the OH group or a linear or branched alkyl or alkoxy radical having 1 to 6 carbon atoms, $R_{11}$ representing a hydrogen atom or a methyl radical, or a

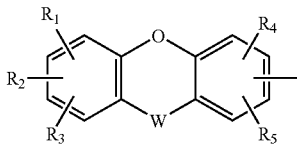

radical in which $R_1$, $R_2$, $R_3$, $R_4$, $R_5$ represent, independently, a hydrogen atom, the OH group or a linear or branched alkyl or alkoxy radical having 1 to 6 carbon atoms;

B represents one of the phenyl, thiophene, furan, pyrrole or thiazole radicals optionally substituted by one or more groups chosen from linear or branched alkyl, alkenyl or alkoxy radicals having 1 to 6 carbon atoms;

W does not exist, or represents a bond, S or $NR_{15}$, in which $R_{15}$ represents a hydrogen atom or a linear or branched alkyl radical having 1 to 6 carbon atoms;

X represents a bond or a $—(CH_2)_k—NR_{16}—$, $—O—$, $—S—$, $—CO—$, $—NR_{16}—CO—$, $—CO—NR_{16}—$, $—O—CO—$, $—CO—O—$, $—NR_{16}—CO—O—$, $—NR_{16}—CO—NR_{17}—$ radical, k representing 0 or 1;

Y represents a bond or a radical chosen from the $—(CH_2)_m—$, $—(CH_2)_m—O—(CH_2)_n—$, $—(CH_2)_m—S—(CH_2)_n—$, $—(CH_2)_m—NR_{18}—(CH_2)_n—$, $—(CH_2)_m—NR_{18}—CO—(CH_2)_n—$, $—(CH_2)_m—CO—NR_{18}—(CH_2)_n—$, $—(CH_2)_m$-Q-$(CH_2)_n—$ radicals, Q representing piperazine, homopiperazine, 2-methylpiperazine, 2,5-dimethylpiperazine, 4-oxypiperidine or 4-aminopiperidine, m and n being integers comprised from 0 to 6;
or are salts of the products mentioned previously.

Yet more preferentially, the compounds according to the invention are compounds of general formula (I) such that:
A represents a

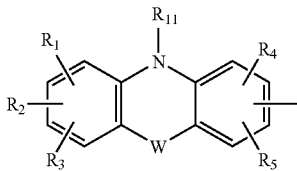

radical in which $R_1$, $R_2$, $R_3$, $R_4$, $R_5$ represent, independently, a hydrogen atom or a methyl radical,
$R_{11}$ representing a hydrogen atom or a methyl radical;

B represents the thiophene radical;

W does not exist, represents a single bond or S;

X represents a bond or represents a $—(CH_2)_k—NR_{16}—$, $—O—$, $—S—$, $—CO—$, $—NR_{16}—CO—$, $—CO—NR_{16}—$, $—O—CO—$, $—CO—O—$, $—NR_{16}—CO—O—$, $—NR_{16}—CO—NR_{17}—$ radical;

k representing 0 or 1;

Y represents a bond or a radical chosen from the $—(CH_2)_m—$, $—(CH_2)_m—O—(CH_2)_n—$, $—(CH_2)_m—S—(CH_2)_n—$, $—(CH_2)_m—NR_{18}—(CH_2)_n—$, $—(CH_2)_m—NR_{18}—CO—(CH_2)_n—$, $—(CH_2)_m—CO—NR_{18}—(CH_2)_n—$, $—(CH_2)_m$-Q-$(CH_2)_n—$ radicals, Q representing piperazine, m and n being integers comprised between 0 and 6;

$R_{16}$, $R_{17}$ and $R_{18}$ represent a hydrogen atom;
or are salts of the products mentioned previously.

Quite particularly preferred are the following compounds described in the examples:

N-[4-(phenylamino)phenyl]-2-thiophenecarboximidamide;
4-{[2-thienyl(imino)methyl]amino}-N-[4-(phenylamino)phenyl]-benzeneacetamide;
{4-{[2-thienyl(imino)methyl]amino}phenoxy}-N-[4-(phenylamino)phenyl]-acetamide;
4-{[2-thienyl(imino)methyl]amino}-N-[2-(phenylamino)phenyl]-benzenebutanamide;
4-{[2-thienyl(imino)methyl]amino}-N-[4-(phenylamino)phenyl]-benzenebutanamide;
4-{[2-thienyl(imino)methyl]amino}-N-[4-(4-methoxyphenylamino)phenyl]-benzenebutanamide;
2-{4-{[2-thienyl(imino)methyl]amino}phenyl}-ethyl[4-(phenylamino)phenyl]-carbamate;
N-{2-{4-{[2-thienyl(imino)methyl]amino}phenyl}ethyl}-N'-[4-(phenylamino)phenyl]-urea;
4-{4-{[2-thienyl(imino)methyl]amino}phenyl}-N-[4-(phenylamino)phenyl]-1-piperazine-acetamide;
1-{[(4-phenylamino)phenylamino]carbonyl}-4-{4-{[2-thienyl(imino)methyl]amino}phenyl}-piperazine;
4-{[2-thienyl(imino)methyl]amino}-N-[4-(phenylamino)phenyl]-benzenebutanamine;
3-{[2-thienyl(imino)methyl]amino}-N-[4-(phenylamino)phenyl]-benzenepropanamide;
4-(4-{[amino(2-thienyl)methylidene]amino}phenyl)-N-[2-(4-toluidino)phenyl]butanamide;
4-anilinophenyl-4-(4-{[amino(2-thienyl)methylidene]amino}-phenyl)butanoate;
4-(4-{[amino(2-thienyl)methylidene]amino}phenyl)-N-[2-(4-toluidino)phenyl]butanamide;
N'-{4-[4-(3-anilinophenoxy)butyl]phenyl}-2-thiophenecarboximidamide;
N'-(9H-carbazol-3-yl)-2-thiophenecarboximidamide;
4-(4-{[amino(2-thienyl)methylidene]amino}phenyl)-N-(9H-carbazol-3-yl)butanamide;
N'-[4-(10H-phenothiazin-2-yloxy)phenyl]-2-thiophenecarboximidamide;
N'-{4-[(10-methyl-10H-phenothiazin-2-yl)oxy]phenyl}-2-thiophenecarboximidamide;
4-(4-{[amino(2-thienyl)methylidene]amino}phenyl)-N-(10H-phenothiazin-3-yl)butanamide;
N'-(4-{4-[2-(10H-phenothiazin-2-yloxy)ethyl]-1-piperazinyl}phenyl)-2-thiophenecarboximidamide;
4-(4-{[amino(2-thienyl)methylidene]amino}phenyl)-N-[4-(4-toluidino)phenyl]butanamide;
3-anilinophenyl 4-(4-{[amino(2-thienyl)methylidene]amino}-phenyl)butanoate;
2-(4-{[amino(2-thienyl)methylidene]amino}phenyl)-N-[2-(9H-carbazol-4-yloxy)ethyl]acetamide;

N-(4-{[amino(2-thienyl)methylidene]amino}phenethyl)-2-anilinobenzamide;

N-(4-{[amino(2-thienyl)methylidene]amino}phenethyl)-2-(2,3-dimethylanilino)benzamide;

N'-{4-[4-(2-anilinobenzoyl)-1-piperazinyl]phenyl}-2-thiophenecarboximidamide;

N'-(4-{4-[2-(2,3-dimethylanilino)benzoyl]-1-piperazinyl}phenyl)-2-thiophenecarboximidamide;

4-(4-{[amino(2-thienyl)methylidene]amino}phenyl)-N-(4-phenoxyphenyl)butanamide;

N-(4-{[amino(2-thienyl)methylidene]amino}phenethyl)-4-(4-hydroxyphenoxy)benzamide;

N-[2-(9H-carbazol-4-yloxy)ethyl]-2-thiophenecarboximidamide;

N-[3-(9H-carbazol-4-yloxy)propyl]-2-thiophenecarboximidamide;

N-{4-[4-(10H-phenothiazin-2-yloxy)butyl]phenyl}-2-thiophenecarboximidamide;

3-[(3-{[amino(2-thienyl)methylidene]amino}-benzyl)amino]-N-(4-anilinophenyl)propanamide;

N'-(4-{2-[(10H-phenothiazin-3-ylmethyl)amino]ethyl}phenyl)-2-thiophenecarboximidamide;

N-(4-{[amino(2-thienyl)methylidene]amino}phenethyl)-2-methoxy-10H-phenothiazine-1-carboxamide;

N'-[4-(2-{[(2-methoxy-10H-phenothiazin-1-yl)methyl]amino}ethyl)phenyl]-2-thiophenecarboximidamide;

N'-{4-[(10H-phenothiazin-2-yloxy)methyl]phenyl}-2-thiophenecarboximidamide;

or their salts.

Among the exemplified compounds, the following compounds are in particular preferred:

{4-{[2-thienyl(imino)methyl]amino}phenoxy}-N-[4-(phenylamino)phenyl]-acetamide;

4-{[2-thienyl(imino)methyl]amino}-N-[2-(phenylamino)phenyl]-benzenebutanamide;

4-{[2-thienyl(imino)methyl]amino}-N-[4-(phenylamino)phenyl]-benzenebutanamide;

2-{4-{[2-thienyl(imino)methyl]amino}phenyl}-ethyl[4-(phenylamino)phenyl]-carbamate;

4-{4-{[2-thienyl(imino)methyl]amino}phenyl}-N-[4-(phenylamino)phenyl]-1-piperazine-acetamide;

3-{[2-thienyl(imino)methyl]amino}-N-[4-(phenylamino)phenyl]-benzenepropanamide;

4-(4-{[amino(2-thienyl)methylidene]amino}phenyl)-N-[2-(4-toluidino)phenyl]butanamide;

N'-{4-[4-(3-anilinophenoxy)butyl]phenyl}-2-thiophenecarboximidamide;

4-(4-{[amino(2-thienyl)methylidene]amino}phenyl)-N-(9H-carbazol-3-yl)butanamide;

N'-[4-(10H-phenothiazin-2-yloxy)phenyl]-2-thiophenecarboximidamide;

4-(4-{[amino(2-thienyl)methylidene]amino}phenyl)-N-(10H-phenothiazin-3-yl)butanamide;

N'-(4-{4-[2-(10H-phenothiazin-2-yloxy)ethyl]-1-piperazinyl}phenyl)-2-thiophenecarboximidamide;

4-(4-{[amino(2-thienyl)methylidene]amino}phenyl)-N-(4-phenoxyphenyl)butanamide;

3-[(3-{[amino(2-thienyl)methylidene]amino}-benzyl)amino]-N-(4-anilinophenyl)propanamide;

N'-(4-{2-[(10H-phenothiazin-3-ylmethyl)amino]ethyl}phenyl)-2-thiophenecarboximidamide;

N-(4-{[amino(2-thienyl)methylidene]amino}phenethyl)-2-methoxy-10H-phenothiazine-1-carboxamide;

or their salts.

Also more particularly the following compounds are preferred:

4-{[2-thienyl(imino)methyl]amino}-N-[2-(phenylamino)phenyl]-benzenebutanamide;

4-{[2-thienyl(imino)methyl]amino}-N-[4-(phenylamino)phenyl]-benzenebutanamide;

N'-[4-(10H-phenothiazin-2-yloxy)phenyl]-2-thiophenecarboximidamide;

4-(4-{[amino(2-thienyl)methylidene]amino}phenyl)-N-(10H-phenothiazin-3-yl)butanamide;

3-[(3-{[amino(2-thienyl)methylidene]amino}-benzyl)amino]-N-(4-anilinophenyl)propanamide;

N'-(4-{2-[(10H-phenothiazin-3-ylmethyl)amino]ethyl}phenyl)-2-thiophenecarboximidamide;

or their salts.

In a general manner, the compounds of general formula (I) in which X represents a bond or one of the —O—, —CH$_2$—NR$_{16}$—, —NR$_{16}$—CO— or —NR$_{16}$—CO—O-radicals and Y represents one of the —(CH$_2$)$_m$— or —(CH$_2$)$_m$—NR$_{18}$—(CH$_2$)$_n$— radicals will be preferred.

In certain cases, the compounds according to the present invention can contain asymmetrical carbon atoms. As a result, the compounds according to the present invention have two possible enantiomeric forms, i.e. "R" and "S" configurations. The present invention includes the two enantiomeric forms and all combinations of these forms, including the racemic "RS" mixtures. In an effort to simplify matters, when no specific configuration is indicated in the structural formulae, it should be understood that the two enantiomeric forms and their mixtures are represented.

The invention further relates, as new industrial products, to the synthesis intermediates of general formula (IS), useful for the preparation of products of general formula (I) defined above,

A-X—Y-Φ-T    (IS)

general formula (IS) in which

A represents a

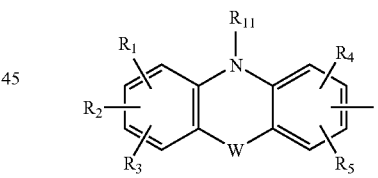

radical in which R$_1$, R$_2$, R$_3$, R$_4$, R$_5$ represent, independently, a hydrogen atom, a halogen, the OH group, a linear or branched alkyl or alkoxy radical having 1 to 6 carbon atoms, or a cyano, nitro or NR$_6$R$_7$ radical, R$_6$ and R$_7$ representing, independently, a hydrogen atom, the OH group, a linear or branched alkyl or alkoxy radical having 1 to 6 carbon atoms, or also a —COR$_8$ group, R$_8$ representing a hydrogen atom, the OH group, a linear or branched alkyl or alkoxy radical having 1 to 6 carbon atoms, or NR$_9$R$_{10}$, R$_9$ and R$_{10}$ representing, independently, a hydrogen atom, the OH group or a linear or branched alkyl radical having 1 to 6 carbon atoms, R$_{11}$ representing a hydrogen atom, the OH group, a linear or branched alkyl or alkoxy radical having 1 to 6 carbon atoms, or a —COR$_{12}$ radical, and R$_{12}$ representing a hydrogen atom, the OH group, a linear or branched alkyl radical having 1 to 6 carbon atoms, or a

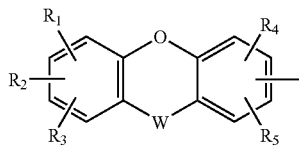

radical in which R$_1$, R$_2$, R$_3$, R$_4$, R$_5$ represent, independently, a hydrogen atom, a halogen, the OH group, a linear or branched alkyl or alkoxy radical having 1 to 6 carbon atoms, or a cyano, nitro or NR$_6$R$_7$ radical, R$_6$ and R$_7$ representing, independently, a hydrogen atom, the OH group, a linear or branched alkyl or alkoxy radical having 1 to 6 carbon atoms, or also a —COR$_8$ group, R$_8$ representing a hydrogen atom, the OH group, a linear or branched alkyl or alkoxy radical having 1 to 6 carbon atoms, or NR$_9$R$_{10}$, R$_9$ and R$_{10}$ representing, independently, a hydrogen atom, the OH group or a linear or branched alkyl radical having 1 to 6 carbon atoms;

W does not exist, or represents a bond, or O, S or NR$_{15}$, in which R$_{15}$ represents a hydrogen atom or a linear or branched alkyl radical having 1 to 6 carbon atoms;

X represents a bond or a —(CH$_2$)$_k$—NR$_{16}$—, —O—, —S—, —CO—, —NR$_{16}$—CO—, —CO—NR$_{16}$—, —O—CO—, —CO—O—, —NR$_{16}$—CO—O— or —NR$_{16}$—CO—NR$_{17}$— radical, k representing 0 or 1;

Y represents a bond or a radical chosen from the —(CH$_2$)$_m$—, —(CH$_2$)$_m$—O—(CH$_2$)$_n$—, (CH$_2$)$_m$—S—(CH$_2$)$_n$—, —(CH$_2$)$_m$—NR$_{18}$—(CH$_2$)$_n$—, —(CH$_2$)$_m$—NR$_{18}$—CO—(CH$_2$)$_n$—, —(CH$_2$)$_m$—CO—NR$_{18}$—(CH$_2$)$_n$, —(CH$_2$)$_m$-Q-(CH$_2$)$_n$— radicals, Q representing piperazine, homopiperazine, 2-methylpiperazine, 2,5-dimethylpiperazine, 4-oxypiperidine or 4-aminopiperidine, m and n being integers from 0 to 6;

Φ represents a bond or a phenylene radical which may comprise, in addition to the two chains already represented in general formula (I), up to two substituents chosen from a hydrogen atom, a halogen, an OH group and a linear or branched alkyl or alkoxy radical having 1 to 6 carbon atoms;

T represents NO$_2$ or NH$_2$;

R$_{16}$, R$_{17}$ and R$_{18}$ represent, independently, a hydrogen atom or a linear or branched alkyl radical having 1 to 6 carbon atoms.

The invention further relates, as new industrial products, to the synthesis intermediates of general formula (IS'), useful for the preparation of products of general formula (I) in which X represents the —NR$_{16}$—CO— radical and Y represents the —(CH$_2$)$_m$—NR$_{18}$—(CH$_2$)$_n$— radical,

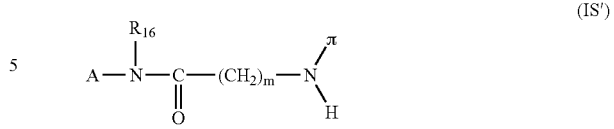

general formula (IS') in which

A represents a

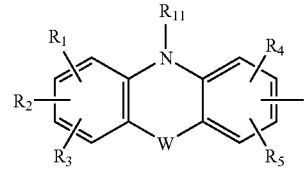

radical in which R$_1$, R$_2$, R$_3$, R$_4$ and R$_5$ represent, independently, a hydrogen atom, a halogen, the OH group, a linear or branched alkyl or alkoxy radical having 1 to 6 carbon atoms, or a cyano, nitro or NR$_6$R$_7$ radical, R$_6$ and R$_7$ representing, independently, a hydrogen atom, the OH group, a linear or branched alkyl or alkoxy radical having 1 to 6 carbon atoms, or also a —COR$_8$ group, R$_8$ representing a hydrogen atom, the OH group, a linear or branched alkyl or alkoxy radical having 1 to 6 carbon atoms, or NR$_9$R$_{10}$, R$_9$ and R$_{10}$ representing, independently, a hydrogen atom, the OH group, a linear or branched alkyl radical having 1 to 6 carbon atoms, R$_{11}$ representing a hydrogen atom, the OH group, a linear or branched alkyl or alkoxy radical having 1 to 6 carbon atoms, or also a —COR$_{12}$ radical, and R$_{12}$ representing a hydrogen atom, the OH group, a linear or branched alkyl radical having 1 to 6 carbon atoms, or a

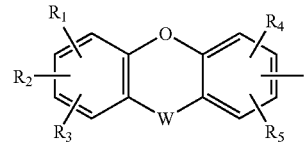

radical in which R$_1$, R$_2$, R$_3$, R$_4$, R$_5$ represent, independently, a hydrogen atom, a halogen, the OH group, a linear or branched alkyl or alkoxy radical having 1 to 6 carbon atoms, or a cyano, nitro or NR$_6$R$_7$ radical, R$_6$ and R$_7$ representing, independently, a hydrogen atom, the OH group, a linear or branched alkyl or alkoxy radical having 1 to 6 carbon atoms, or also a —COR$_8$ group, R$_8$ representing a hydrogen atom, the OH group, a linear or branched alkyl or alkoxy radical having 1 to 6 carbon atoms, or NR$_9$R$_{10}$, R$_9$ et R$_{10}$ representing, independently, a hydrogen atom, the OH group, a linear or branched alkyl radical having 1 to 6 carbon atoms;

W does not exist, or represents a bond, or O, S or NR$_{15}$, in which R$_{15}$ represents a hydrogen atom or a linear or branched alkyl radical having 1 to 6 carbon atoms;

π represents a hydrogen atom or a protective group of the carbamate type;

$R_{16}$, $R_{17}$ and $R_{18}$ represent, independently, a hydrogen atom or a linear or branched alkyl radical having 1 to 6 carbon atoms;

and m represents an integer from 0 to 6.

A subject of the invention is also, as medicaments, the compounds of general formula (I) described previously or their pharmaceutically acceptable salts. It also relates to pharmaceutical compositions containing these compounds or their pharmaceutically acceptable salts, and the use of these compounds or of their pharmaceutically acceptable salts for producing medicaments intended to inhibit neuronal NO synthase or inductible NO synthase, to inhibit lipidic peroxidation or to provide the double function of NO synthase inhibition and lipidic peroxidation inhibition.

By pharmaceutically acceptable salt is meant in particular addition salts of inorganic acids such as hydrochloride, hydrobromide, hydroiodide sulphate, phosphate, diphosphate and nitrate, or of organic acids, such as acetate, maleate, fumarate, tartrate, succinate, citrate, lactate, methanesulphonate, p-toluenesulphonate, parnoate, oxalate and stearate. The salts formed from bases such as sodium or potassium hydroxide also fall within the scope of the present invention, when they can be used. For other examples of pharmaceutically acceptable salts, reference can be made to "Pharmaceutical salts", *J. Pharm. Sci.* 66:1 (1977).

The pharmaceutical composition can be in the form of a solid, for example powders, granules, tablets, capsules, liposomes or suppositories. Appropriate solid supports can be for example calcium phosphate, magnesium stearate, talc, sugars, lactose, dextrin, starch, gelatin, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or the glycols, as well as their mixtures, in varying proportions, in water.

A medicament according to the invention can be administered by topical, oral or parenteral route, by intramuscular injection, etc.

The envisaged administration dose for a medicament according to the invention is comprised between 0.1 mg and 10 g according to the type of active compound used.

In accordance with the invention, the compounds of general formula (I) can be prepared by the process described below.

PREPARATION OF THE COMPOUNDS OF GENERAL FORMULA (I)

The compounds of general formula (I) can be prepared from intermediates of general formula (II) according to Diagram 1 where A, B, X, Y and Φ are as defined above and Gp is a protective group of carbamate type such as for example the t-butoxycarbonyl group.

Diagram 1

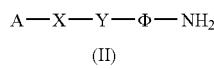

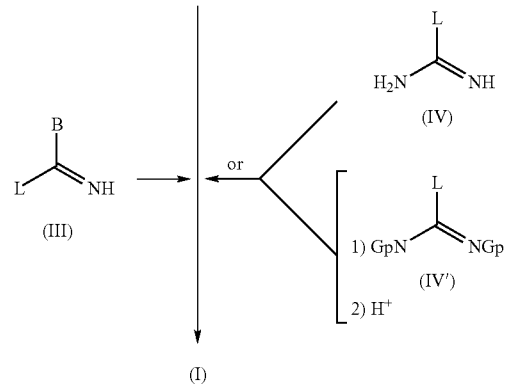

The derivatives of aniline of general formula (II), can be condensed with the compounds of general formula (III), in which L represents a parting group (for example an alkoxy, alkylthio, aralkylthio, sulphonic acid, halide, aryl alcohol or tosyl radical), in order to produce the final compounds of general formula (I) of substituted amidine type (cf. Diagram 1). For example, for B=thiophene, the derivatives of general formula (II) can be condensed with S-methylthiophene thiocarboxamide hydroiodide, prepared according to a method in the literature (*Ann. Chim.* (1962), 7, 303–337). The condensation can be carried out by heating in an alcohol (for example in methanol or isopropanol), optionally in the presence of DMF and/or pyridine at a temperature preferably comprised between 20 and 100° C. for a duration generally comprised between a few hours and overnight.

In the case where B is an amine, the final compounds of general formula (I) are guanidines. These can be prepared, for example, by the condensation of the amines of general formula (II) with the derivatives of general formula (IV) or (IV'). The reagents of general formula (IV) in which L represents, for example, a pyrazole ring are condensed with the amines of general formula (II) according to the conditions described in the literature (*J. Org. Chem.* (1992) 57, 2497–2502) similarly for the reagents of general formula (IV') in which L represents, for example, a pyrazole ring and Gp the tBuOCO group (*Tetrahedron Lett.* (1993) 34 (21), 3389–3392) or when L represents the —N—SO₂—CF₃ group and Gp the tBuOCO group (*J. Org. Chem.* (1998) 63, 3804–3805). During the final stage of the synthesis, deprotection of the guanidine function is carried out in the presence of a strong acid such as for example trifluoroacetic acid.

Therefore the invention also relates to a process for the preparation of a product of general formula (I) as defined previously, characterized in that intermediate of general formula (II)

A-X—Y-Φ-NH₂ (II)

in which A, X, Y and Φ are as defined above, is reacted with intermediate of general formula (III)

in which B is as defined above and L represents a parting group, for example an alkoxy, alkylthio, aralkylthio, sulphonic acid, halide, aryl alcohol or tosyl radical.

In addition the invention relates to a process for the preparation of a product of general formula (I) in which B is an amine, characterized in that intermediate of general formula (II)

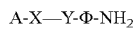  (II)

in which A, B, X, Y and Φ are as defined above is reacted,
a) either with intermediate of general formula (IV)

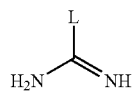  (IV)

in which L represents a parting group, for example an alkoxy, alkylthio, aralkylthio, sulphonic acid, halide, aryl alcohol or tosyl radical,
b) or with intermediate of general formula (IV')

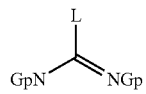  (IV')

in which L represents a parting group, for example an alkoxy, alkylthio, aralkylthio, sulphonic acid, halide, aryl alcohol or tosyl radical, and Gp a protective group of carbamate type, for example the t-butoxycarbonyl group,
this reaction being followed, in the case where reaction with the compound of general formula (IV') is chosen, by hydrolysis in the presence of a strong acid, for example trifluoroacetic acid.

When —X—Y-Φ-Represents a Direct Bond:

Intermediates of general formula (II) in the particular case where —X—Y-Φ-represents a direct bond are comparable to the compounds of general formula (X), A-NH$_2$, described in the chapter "Synthesis of intermediates". In this case, these A-NH$_2$ amines can be directly condensed with the derivatives of general formula (III) or (IV) as described in the preceding chapter.

Prepartion of the Compounds of General Formula (II)

The non-commercial intermediates of general formula (II), are obtained either from detachment of a protective group, or from reduction of a precursor of nitride or nitro type, as illustrated in the synthesis diagrams below.

Deprotection of the Amino Group:

Intermediates of general formula (II), in which A, X, Y and Φ are as defined above, can be prepared from intermediates of general formula (V), Diagram 2, which are compounds comprising a protected amine (N=Gp') in the form, for example, of phthalimide or 2,5-dimethylpyrrole. In the case of phthalimides, these are deprotected in a standard fashion using hydrazine hydrate under reflux of ethanol and in the case of pyrroles, deprotection takes place by heating in the presence of hydroxylamine hydrochloride, in order to finally produce to the primary amines of general formula (II).

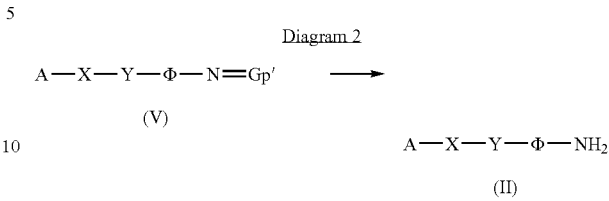

Reduction of the Precursors of Azido Type:

The synthetic intermediates of general formula (VI), Diagram 3, in which A, X, Y and Φ are as defined above, are azide derivatives which are converted into a primary amine of general formula (II), for example, using hydrogen in the presence of Pd/C in an appropriate solvent such as ethanol.

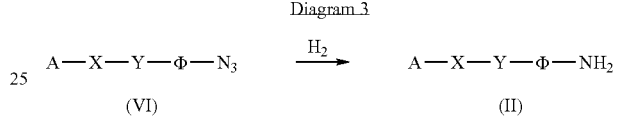

Reduction of the Precursors of Nitro Type:

The reduction of the nitro function of intermediates of general formula (VII), Diagram 4, in which A, X, Y and Φ are as defined above, is generally carried out by catalytic hydrogenation, in ethanol, in the presence of Pd/C, except in the case of molecules sensitive to these conditions where the nitro group is selectively reduced, for example, by heating the product in an appropriate solvent such as ethyl acetate with a little ethanol in the presence of SnCl$_2$ (*J. Heterocyclic Chem.* (1987), 24, 927–930; *Tetrahedron Letters* (1984), 25 (8), 839–842), also using SnCl$_2$ in the presence of Zn (*Synthesis* (1996), (9), 1076–1078), or using NaBH$_4$—BiCl$_3$ (*Synth. Com.* (1995) 25 (23), 3799–3803) in a solvent such as ethanol, or then by using Raney Ni with hydrazine hydrate added (*Monatshefte für Chemie*, (1995), 126, 725–732; *Pharmazie* (1993) 48 (11), 817–820) in the case, for example, of the nitrocarbazoles.

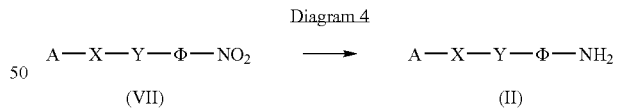

Preparation of the Compounds of General Formula (V):

Intermediates of general formula (V), Diagram 5, contain an amine protected in the form of phthalimide, in which X=—O—, Y=—(CH$_2$)$_m$— with A, R$_1$, R$_2$, R$_3$, R$_4$, R$_5$, W, m and Φ as defined above, can be prepared from the hydroxylated aromatic rings of general formula (VIII). In the particular case of hydroxycarbazoles, the compounds of general formula (VIII) are prepared according to an experimental protocol in the literature (*J. Chem. Soc.* (1955), 3475–3477; *J. Med. Chem.* (1964) 7, 158–161) and in that of hydroxyphenothiazines the protocol is described in *J. Med. Chem.* (1992) 35, 716. The compounds of general formula (VIII) are condensed with commercial halogenoalkyl-phthalimides in the presence of a base, for example NaH, in a solvent such as DMF, in order to produce intermediates of general formula (V).

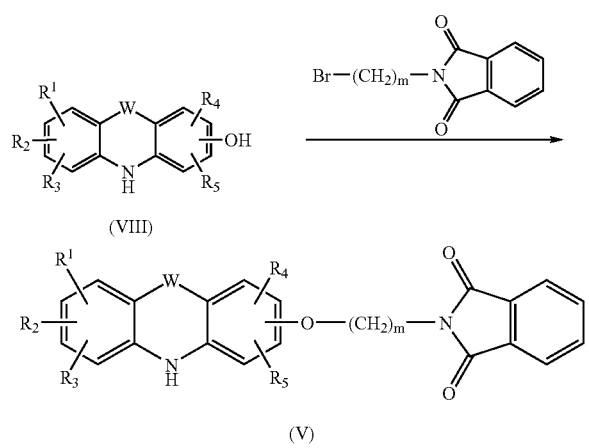

Diagram 5

(VIII)

(V)

Preparation of the Compounds of General Formula (VI):

Intermediates of general formula (VI), Diagram 6, in which A, X, Y, $R_1$, $R_2$, $R_3$, $R_4$, $R_5$, W, m and Φ are as defined above, are derivatives of azido type. They are prepared in two stages from intermediates of general formula (VIII) (Diagram 5). The OH radical of the compounds of general formula (VIII) can be alkylated by dihalogenated derivatives of dibromoalkane type, in the presence of a base, for example NaH or NaOH, in order to produce the compounds of general formula (IX) which are then substituted using sodium azide in DMF in order to produce intermediates of general formula (VI).

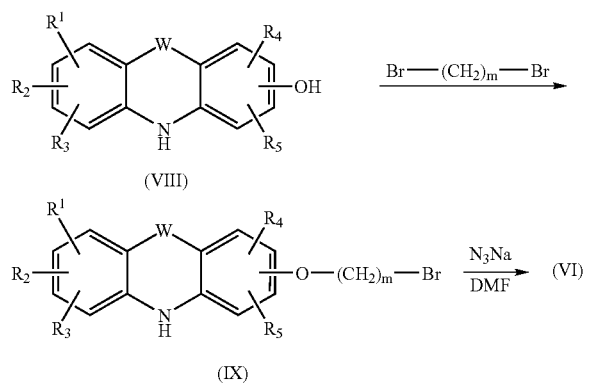

Diagram 6

(VIII)

(IX)

Preparation of the Compounds of General Formula (VII):

The syntheses of the compounds of general formula (VII), which carry a terminal nitro group, in which A, X, Y and Φ are as described above, are illustrated in the following synthesis diagrams.

Syntheses of the Carboxamides of General Formula (VII):

The carboxamides of general formula (VII), Diagram 7, in which X represents —$NR_{16}$—CO— and A, Y, Φ and $R_{16}$ are as defined above, are prepared by condensation of the commercial amines of general formula (X) with the commercial acids of general formula (XI). The carboxamide bonds are formed under the standard conditions of peptide synthesis (M. Bodanszky and A. Bodanszky, The Practice of Peptide Synthesis, 145 (Springer-Verlag, 1984)) in THF, dichloromethane or DMF in the presence of a coupling reagent such as dicyclohexylcarbodiimide (DCC), 1.1'-carbonyldiimidazole (CDI) (J. Med. Chem. (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)). The syntheses of the non-commercial amines of general formula (X) and the syntheses of the non-commercial carboxylic acids of general formula (XI) are described in the chapter Preparation of Intermediates.

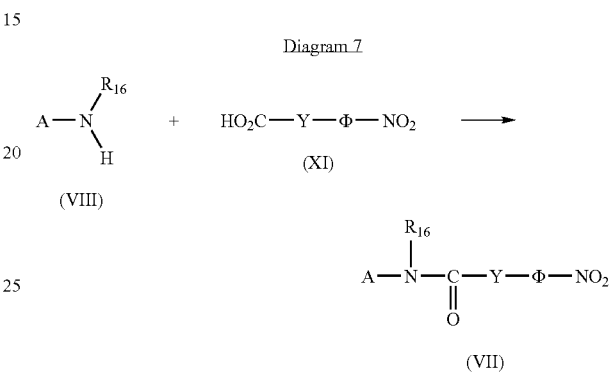

Diagram 7

(VIII) (XI)

(VII)

The carboxamides of general formula (VII), Diagram 8, in which X represents —CO—$NR_{16}$— and A, Y, Q, Φ and $R_{16}$ are as defined above, are prepared by condensation of the commercial acids of general formula (XII) with the commercial amines of general formula (XIII) or the amines of general formula (XIV) under standard conditions for peptide synthesis described previously. The syntheses of the non-commercial acids of general formula (XII) and amines of general formula (XIV) are described in the chapter Preparation of Intermediates.

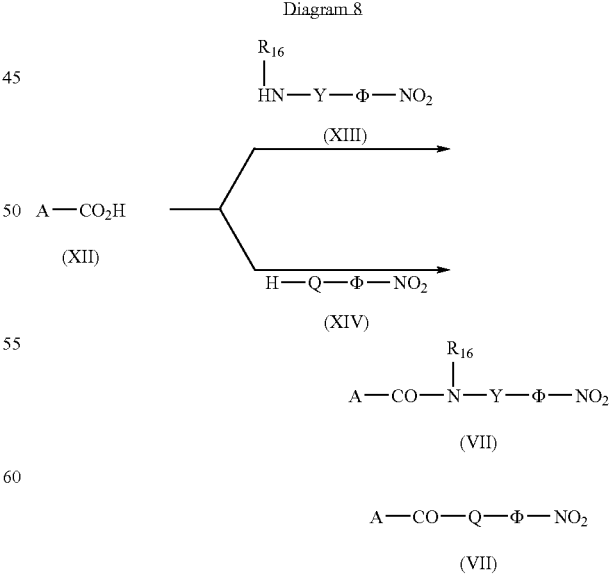

Diagram 8

(XIII)

(XII)

(XIV)

(VII)

(VII)

The carboxamides of general formula (VII), Diagram 9, in which X represents —O—, Y represents —$(CH_2)_m$—

$NR_{18}$—CO—$(CH_2)_n$— with A, $R_{18}$, m, n and Φ as defined above, are prepared by standard peptide condensation of the acids of general formula (XI) (Diagram 7) with the amines of general formula (II), the syntheses of which have been described in Diagrams 2 and 3.

Diagram 9

$$A-O-(CH_2)_m-\underset{R_{18}}{\underset{|}{N}}H + HO_2C-Y-\Phi-NO_2 \longrightarrow$$

(II)  (XI)

$$A-O-(CH_2)_m-\underset{R_{18}}{\underset{|}{N}}-\underset{\|}{\underset{O}{C}}-Y-\Phi-NO_2$$

(VII)

Synthesis of the Amines of General Formula (VII):

The amines of general formula (VII) in which X=—$NR_{16}$— and Y=—$(CH_2)_m$— with A, $R_{16}$, m and Φ as defined above, are prepared, Diagram 10, from the carboxamides of general formula (VII). The reduction of the carboxamide function is carried out in the presence of an excess (5 eq.) of diborane in THF, by heating, the mixture to reflux of the solvent in order to produce the amines of general formula (VII).

Diagram 10

$$A-\underset{R_{16}}{\underset{|}{N}}-\underset{\|}{\underset{O}{C}}-Y-\Phi-NO_2 \longrightarrow$$

(VII)

$$A-\underset{R_{16}}{\underset{|}{N}}-\underset{H\ \ H}{C}-Y-\Phi-NO_2$$

(VII)

Synthesis of the Carbamates of General Formula (VII):

The carbamate derivatives of general formula (VII) in which X=—$NR_{16}$—CO—O— and Y=—$(CH_2)_m$— with A, m and Φ as defined above, are prepared, Diagram 11, by condensation of an amine of general formula (X) (Diagram 7) with a commercial alcohol of general formula (XV) in the presence of triphosgene and a base such as for example N,N-dimethylaniline in an inert solvent such as, for example, dichloromethane, according to a protocol described in *Tetrahedron Lett.* (1993) 34 (44), 7129–7132.

Diagram 11

$$A-NH_2 + HO-Y-\Phi-NO_2 \xrightarrow{Triphosgene}$$

(X)  (XV)

-continued $$A-\underset{H}{\underset{|}{N}}-\underset{\|}{\underset{O}{C}}-O-Y-\Phi-NO_2$$

(VII)

Synthesis of the Ureas of General Formula (VII):

The ureas of general formula (VII) in which X=—$NR_{16}$—CO—$NR_{17}$— and Y=—$(CH_2)_m$— or X—Y=—$NR_{16}$—CO-Q- (in the case of a nitrogenous heterocycle) with A, $R_{17}$, m, Q and Φ as defined above, are prepared, Diagram 12, from the primary amines of general formula (X) (Diagram 7) and the amines of general formula (XIII) or (XIV) (Diagram 8) in the presence of triphosgene and a tertiary amine, such as, for example, diisopropylethylamine, in a neutral solvent such as dichloromethane (*J. Org. Chem.* (1994), 59 (7), 1937–1938).

Diagram 12

$$A-NH_2 + HN-\underset{R_{17}}{\underset{|}{}}-Y-\Phi-NO_2 \xrightarrow{Triphosgene}$$

(X)  (XIII)

$$A-\underset{H}{\underset{|}{N}}-\underset{\|}{\underset{O}{C}}-\underset{R_{17}}{\underset{|}{N}}-Y-\Phi-NO_2$$

(VII)

$$A-NH_2 + H-Q-\Phi-NO_2 \xrightarrow{Triphosgene}$$

(X)  (XIV)

$$A-\underset{H}{\underset{|}{N}}-\underset{\|}{\underset{O}{C}}-Q-\Phi-NO_2$$

(VII)

Synthesis of the Esters of General Formula (VII):

The carboxylic esters of general formula (VII) in which X=—O—CO— or —CO—O— and Y=—$(CH_2)_m$— with A, m and Φ as defined above, are prepared in a single stage from the alcohols of general formula (VIII) (Diagram 5) and the carboxylic acids of general formula (XI) (Diagram 7) or the acids of general formula (XII) (Diagram 8) and the alcohols of general formula (XV) (Diagram 11) in the presence of a coupling agent such as, for example carbonyldiimidazole or dicyclohexylcarbodiimide, in an appropriate solvent such as dichloromethane, for example.

Diagram 13

$$A-OH + HO_2C-Y-\Phi-NO_2 \longrightarrow$$

(VIII)  (XI)

-continued

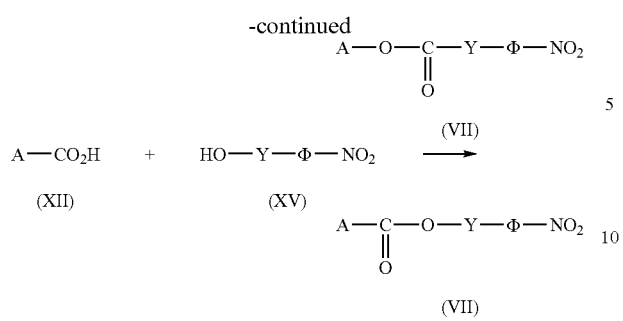

Synthesis of the Esthers of General Formula (VII):

The ethers of general formula (VII) in which X=—O— and Y=—(CH$_2$)$_m$— with A, m and Φ as defined above, Diagram 14, are prepared in a single stage by condensation of the aromatic alcohols of general formula (VIII) (Diagram 5) and the alcohols of general formula (XV) (Diagram 11) under the standard conditions of Mitsunobu (*Synthesis* (1981), 1) in the presence, for example, of diethylazodicarboxylate and tributylphosphine, in a solvent such as, for example, THF.

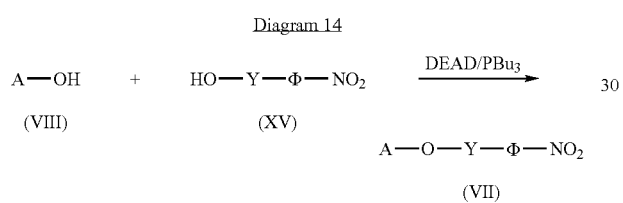

When X=—O—, Y is a bond and Φ=phenylene, with A and n as defined above, the ethers of general formula (VII), Diagram 15, can also be prepared in a single stage by condensation of the aromatic alcohols of general formula (VIII) (Diagram 5) with the halogenated derivatives of general formula (XVI), in which Hal represents a halogen atom, in the presence of a base such as, for example, K$_2$CO$_3$, in a polar solvent such as, for example, THF or DMF, at a reaction temperature comprised between 20 and 140° C.

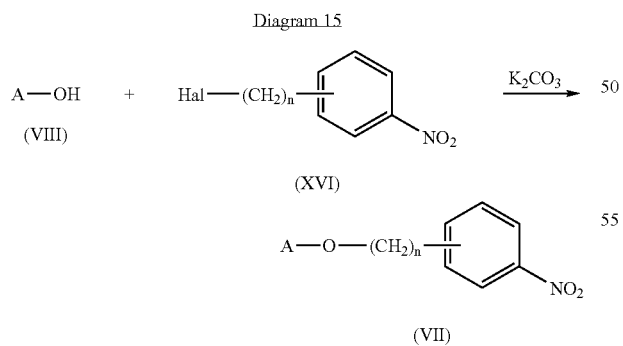

When X=—O— and Y=—(CH$_2$)$_m$-Q-(CH$_2$)$_n$— with A, Φ, Q and m as defined above, the ethers of general formula (VII), Diagram 16, can also be prepared by condensation of the aromatic alcohols of general formula (VIII) (Diagram 5) with the halogenated derivatives of general formula (XVII), in which Hal represents a halogen atom, in the presence of a base such as, for example, K$_2$CO$_3$, in an inert solvent such as, for example, CH$_2$Cl$_2$, at a temperature comprised between 40° C. and the reflux temperature of the reaction mixture. Synthesis of the compounds of general formula (XVII) is described in the chapter Preparation of Intermediates.

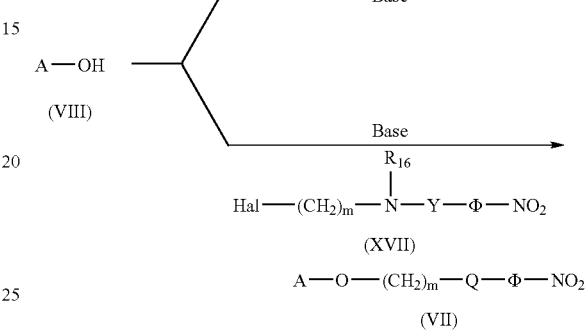

Synthesis of the Amines of General Formula (VII) Amination:

The amines of general formula (VII), in which X=—NR$_{16}$—CO— and Y=—(CH$_2$)$_m$—NR$_{18}$—(CH$_2$)$_n$— with A, Φ, R$_{16}$, R$_{18}$, m and n as defined above, are prepared, Diagram 17, by condensation of an aldehyde of general formula (XIX) with an amine of general formula (XVIII) in reducing medium. The reaction is carried out in an alcoholic solvent such as, for example, methanol in the presence of pulverulent 4 Å molecular sieve, activated beforehand, and of a reducing agent such as, for example, NaBH$_4$ or NaBH$_3$CN. The syntheses of the non-commercial amines of general formula (XVIII) are described in the chapter Preparation of Intermediates.

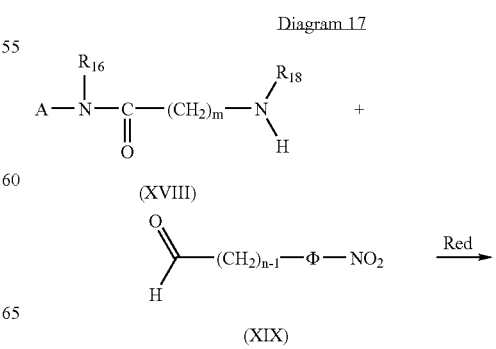

-continued

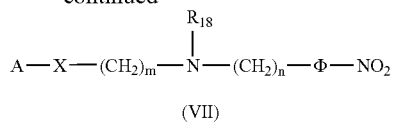

(VII)

In an analogous manner, the amines of general formula (VII), in which X=—CH$_2$—NR$_{16}$—, with A, Y, Φ and R$_{16}$ as defined above, are prepared, Diagram 18, by condensation of the aldehydes of general formula (XX) with the amines of general formula (XIII) (Diagram 8) in reducing medium under the conditions described previously. The preparation of the non-commercial aldehydes of general formula (XX) is described in the chapter Preparation of Intermediates.

Diagram 18

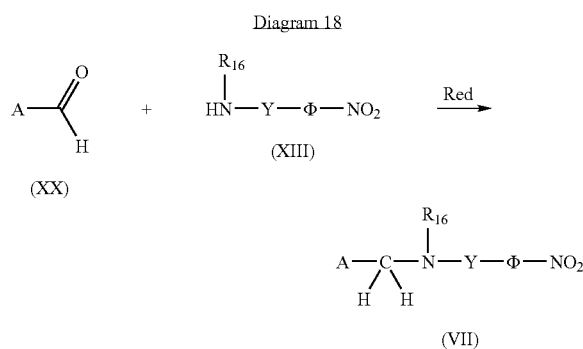

Modification of the a Radical in the Compounds of General Formula (VII)

Intermediates of general formula (VII), in which A, X, Y, Φ, R$_1$, R$_2$, R$_3$, R$_4$ and R$_5$ are as described above, can be subjected to chemical modifications at the level of the A radical, Diagram 19, in particular at the level of the nitrogen atom which can be alkylated using an R$_{11}$-Hal reagent, as defined above, and in particular using methyl iodide in the presence of a base such as, for example, NaH, in an inert solvent such as THF for example.

Diagram 19

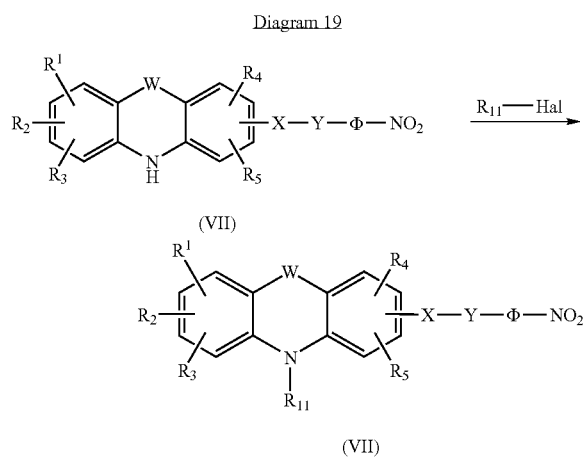

Preparation of the Different Synthesis Intermediates

Synthesis of Intermediates (X):

Intermediates of general formula (X) in which A is a diphenylamine (W does not exist), are accessible using the methods described in the literature (*Synthesis* (1990) 430; *Indian J. Chem.* (1981) 20B, 611–613; *J. Med. Chem.* (1975) 18(4), 386–391) which operate through the reduction of a nitrodiphenylamine intermediate. The reduction of the nitro function is carried out in a standard fashion by hydrogenation in the presence of a catalytic quantity of Pd/C in order to access the aminodiphenylamines of general formula (X).

When A is a carbazole derivative (W then represents a direct bond), the preparation methods for the aminocarbazoles of general formula (X) operate through the synthesis of a nitrocarbazole intermediate. These methods are described in *Pharmazie* (1993) 48(11), 817–820; *Synth. Commun.* (1994) 24(1), 1–10; *J. Org. Chem.* (1980) 45, 1493–1496; *J. Org. Chem.* (1964) 29(8), 2474–2476; *Org Prep. Proced. Int.* (1981) 13(6), 419–421 or *J. Org. Chem.* (1963) 28, 884. The reduction of the nitro function of the nitrocarbazole intermediates is, in this case, preferably carried out using hydrazine hydrate in the presence of Raney Nickel.

Intermediates of general formula (X) in which A is a phenothiazine derivative (W represents a sulphur atom), are accessible via methods in the literature which operate through the synthesis of a nitrophenothiazine derivative. In particular 3-nitrophenothiazine is described in *J. Org Chem.* (1972) 37, 2691. The reduction of the nitro function in order to access the aminophenothiazines of general formula (X) is carried out in a standard fashion by hydrogenation in the presence of a catalytic quantity of Pd/C in a solvent such as ethanol.

Synthesis of Intermediates (XI):

The syntheses of the non-commercial acids of general formula (XI), are described in Diagrams 7.1 and 7.2.

In the particular case where Y=—(CH$_2$)$_m$-Q-(CH$_2$)$_n$— and Φ is a phenylene radical, with Q, m and n as defined above, the carboxylic acids of general formula (XI), Diagram 7.1, are prepared, in 2 stages, from a heterocyclic amine of general formula (XIV) (Diagram 8), for example 4-nitrophenylpiperazine, and of a halogenoester of general formula (XI.1) such as for example ethyl bromoacetate. The condensation is carried out at 20° C. in the presence of a base such as, for example, triethylamine in an inert solvent such as, for example, dichloromethane in order to produce intermediates of general formula (XI.2). Saponification by LiOH at 20° C. produces the carboxylic acids of general formula (XI).

In the cases where Y=—(CH$_2$)$_m$—O—(CH$_2$)$_n$— and Φ is a phenylene radical, with m and n as defined above, the synthesis of the carboxylic acids of general formula (XI), Diagram 7.1, operates through condensation of the halogenated derivatives of general formula (XI.1) on the alcohols of general formula (XI.3) in the presence of a base such as, for example, triethylamine or potassium carbonate, at reflux of a polar solvent such as, for example, THF or DMF. Deprotection of the ester function of intermediate of general formula (XI.4) is then carried out in a standard fashion in the presence of a base or of a strong acid fort in the case of tert-butyl esters.

Diagram 7.1

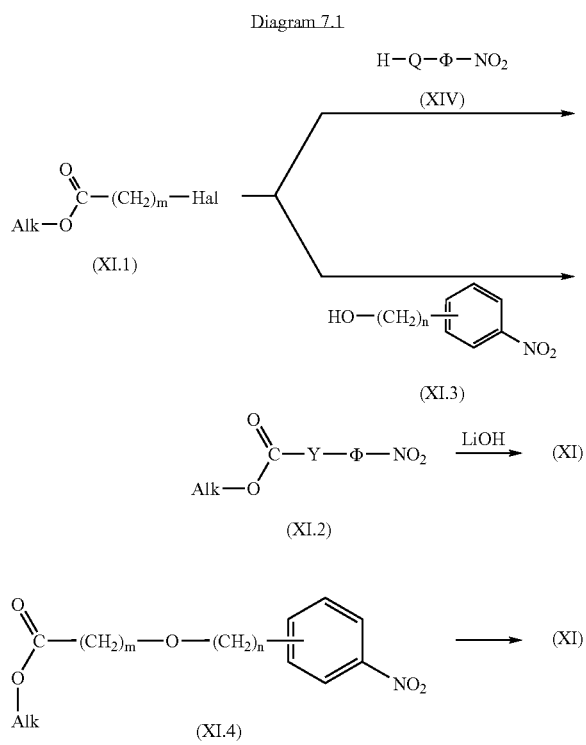

The carboxylic acids of general formula (XI) in which Y=—(CH$_2$)$_m$— and Φ represents a substituted phenylene group, with m as defined above, are prepared in 3 stages from the commercial alcohols of general formula (XI.3), Diagram 7.2. Activation of the alcohol is carried out in a standard fashion using methane sulphonyl chloride (MsCl) in the presence of a base such as triethylamine in an inert solvent such as dichloromethane in order to produce intermediates of general formula (XI.4). The mesylate is then displaced by sodium cyanide in DMF in order to produce intermediates of general formula (XI.5). The nitrile function is then hydrolyzed by heating in a mixture of ethanol and concentrated HCl in order to produce the acids of general formula (XI).

Diagram 7.2

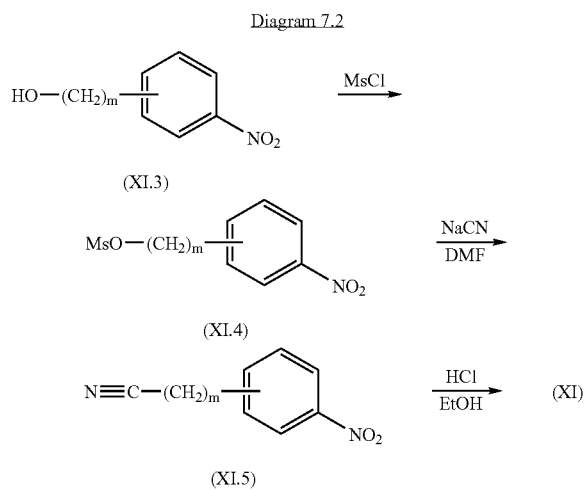

Synthesis of Intermediates (XII):

The synthesis of the carboxylic acid derivatives of the phenothiazines of general formula (XII) is described in literature (*J. Med. Chem.* (1992) 35(4), 716–724).

Synthesis of Intermediates (XIV):

The non-commercial amines of general formula (XIV) defined previously, in which Q represents homopiperazine, 2-methylpiperazine, 2,5-dimethylpiperazine, 4-aminopiperidine, are synthesized in three stages from the corresponding commercial diamines. The diamines are selectively mono-protected in the form of carbamate (*Synthesis* (1984), (12), 1032–1033; *Synth. Commun.* (1990), 20, (16), 2559–2564) before reacting by nucleophilic substitution with a halogeno-nitrobenzene, in particular 4-fluoronitrobenzene. The amines, which have been previously protected, are released at the last stage, according to the methods described in the literature (T. W. Greene and P. G. M. Wuts, *Protective Groups in Organic Synthesis*, Second edition (Wiley-Interscience, 1991)), in order to produce intermediates of general formula (XIV).

Synthesis of Intermediates (XVII):

The halogenated derivatives of general formula (XVII) defined previously, Diagram 16.1, are accessible in two stages from the amines of general formula (XIII) or (XIV) (Diagram 8) and the commercial halogenated derivatives of general formula (XVII.1). Condensation in order to produce intermediates of general formula (XVII.2) or (XVII.3) is carried out in a standard fashion in the presence of a base such as, for example, K$_2$CO$_3$ in an appropriate inert solvent such as, for example, dichloromethane. Then the alcohol function is activated in the form of a halogenated derivative using, for example, carbon tetrabromide in the presence of triphenylphosphine in order to produce intermediates of general formula (XVII).

Diagram 16.1

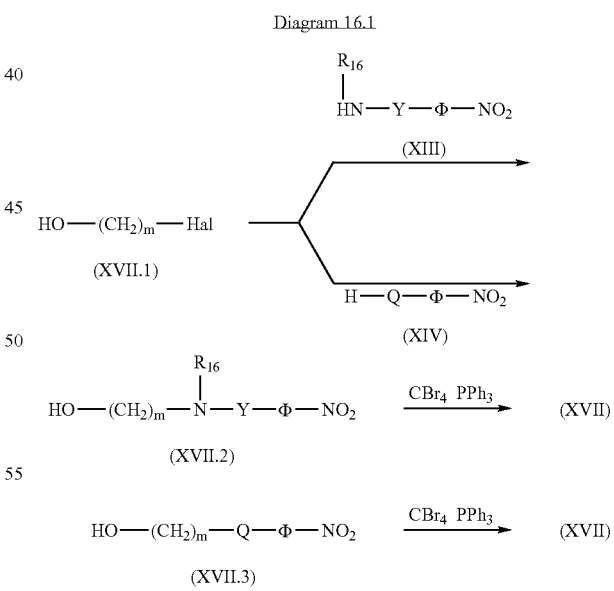

Synthesis of Intermediates (XVIII):

The amines of general formula (XVIII) defined previously, Diagram 17.1, in which A, R$_{16}$, R$_{18}$ and m are as defined above, are prepared by condensation of the amines of general formula (X) (Diagram 7) with the protected amino acids (Gp: protective group) of general formula (XVIII.1), under the standard conditions of peptide synthesis (see "synthesis of carboxamides" chapter). Deprotection of the amine of the compounds of general formula (XVIII.2) is then carried out in a standard fashion according to the conditions described in literature (T. W. Greene et P. G. M. Wuts, *Protective Groups in Organic Synthesis*, Second edition (Wiley-Interscience, 1991)).

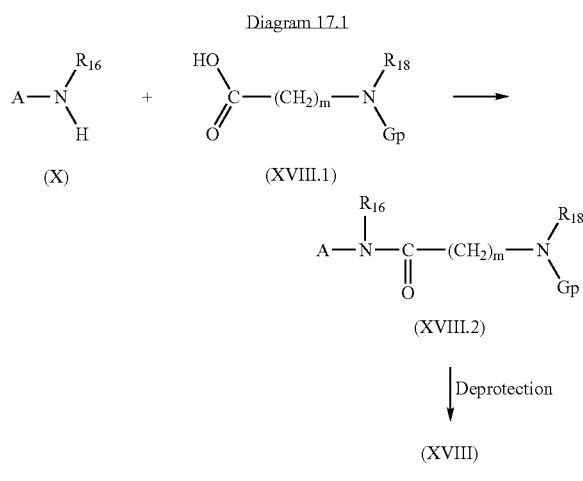

Diagram 17.1

Synthesis of Intermediates (XX):

Synthesis of the aldehydes of the phenothiazines of general formula (XX) defined previously is described in literature (*J. Chem. Soc.* (1951), 1834 ; *Bull. Soc. Chim. Fr.* (1969), 1769).

Unless they are defined differently, all the technical and scientific terms used here have the same meaning as that usually understood by an ordinary specialist in the field to which the invention belongs. Similarly, all publications, patent applications, patents and other references mentioned here are incorporated by way of reference.

The following examples are presented to illustrate the above procedures and should in no way be considered as restricting the scope of the invention.

EXAMPLES

Example 1

N-[4-(phenylamino)phenyl]-2-thiophene-carboximidamide hydroiodide: 1

0.92 g (5 mmol) of 4-aminodiphenylamine and 2.85 g (10 mmol) of S-methyl-2-thiophene thiocarboximide hydroiodide in 15 ml of isopropanol are mixed together in a 50 ml flask under an argon atmosphere. The reaction mixture is heated at 70° C. for 48 hours. The solvent is partially evaporated under vacuum and the solid obtained is filtered and washed several times successively with isopropanol and ethyl ether. A yellow powder is obtained with a yield of 98%. Melting point: 216.3–216.8° C.

NMR $^1$H (400 MHz, DMSO d6, δ): 6.90 (m, 1H, arom.); 7.10–7.30 (m, 8H, arom.); 7.40 (m, 1H, thiophene); 8.10–8.20 (m, 2H, thiophene); 8.50 (s, 1H, NH); 8.75 (s, 1H, NH$^+$); 9.70 (s, 1H, NH$^+$); 11.15 (s, 1H, NH$^+$).

IR: $\nu_{C=N}$ (amidine): 1590 cm$^{-1}$.

Example 2

4-{[2-thienyl(imino)methyl]amino}-N-[4-(phenylamino)phenyl]-benzeneacetamide hydrochloride: 2

2.1)
4-Nitro-N-[4-(phenylamino)phenyl]-benzeneacetamide 1.84 g (10 mmol) of 4-aminodiphenylamine, 1.81 g (10 mmol) of 4-nitrophenylacetic acid and 1.48 g (11 mmol) of hydroxybenzotriazole in 40 ml of THF are dissolved successively in a 100 ml flask. Then 2.27 g (11 mmol) of 1,3-dicyclohexylcarbodiimide (DCC) is added and the reaction mixture is agitated for 15 hours. A precipitate of dicyclohexylurea (DCU) forms which is filtered and rinsed with 100 ml of ethyl acetate. The filtrate is then washed successively with 50 ml of a saturated solution of Na$_2$CO$_3$, 50 ml of water, 50 ml of a molar solution of HCl and finally 2×50 ml of salt water. The organic phase is dried over magnesium sulphate, filtered and concentrated under vacuum. The residue is purified rapidly on a silica gel column (eluent:heptane/ethyl acetate 1/1). The purest fractions are collected and evaporated under vacuum in order to produce a brown powder. The product is used as it is in the following stage.

NMR $^1$H (100 MHz, CDCl$_3$, δ): 1.61 (broad s, 1H, NH); 3.82 (s, 2H, CH$_2$); 5.70 (broad s, 1H, NH); 6.85–7.50 (m, 10H, arom., NH—CO); 7.90 (AB, 4H, Ph-NO$_2$).

2.2)
4-Amino-N-[4-(phenylamino)phenyl]-benzeneacetamide

A solution of intermediate 2.1 (0.54 g, 1.54 mmol) in 40 ml of an ethyl acetate/ethanol mixture (1/1) as well as 0.1 g of Pd/C at 10% are introduced into a stainless steel autoclave equipped with a magnetic stirrer. The reaction mixture is agitated under a hydrogen pressure (1.5 bar) for 1 hour 30 minutes at a temperature of 20° C. The Pd/C is then eliminated by filtration and the filtrate is concentrated under vacuum. The evaporation residue is purified on a silica gel column (eluent:heptane/ethyl acetate: 4/6), the pure fractions are collected and concentrated under vacuum. A white powder is obtained with a yield of 90%. Melting point: 162–163° C.

NMR $^1$H (100 MHz, CDCl$_3$, δ): 1.61 (broad s, 1H, NH); 3.61 (s, 2H, CH$_2$); 3.70 (broad s, 2H, NH$_2$); 5.62 (broad s, 1H, NH—CO); 6.68–7.40 (m, 13H, arom.).

2.3) 4-{[2-thienyl(imino)methyl]amino}-N-[4-(phenylamino)phenyl]-benzeneacetamide hydrochloride: 2

0.44 g (1.39 mmol) of intermediate 2.2 and 0.47 g (1.67 mmol) of S-methyl-2-thiophene thiocarboximide hydroiodide in 15 ml of isopropanol are dissolved in a 50 ml flask. The reaction mixture is agitated for 20 hours at a temperature of 60° C. After evaporation of the solvent under vacuum, the residue is taken up in 100 ml of a mixture of 1N soda and ethyl acetate (1/1). After decantation, the organic phase is washed with 50 ml of water followed by 50 ml of salt water. The organic solution is dried over magnesium sulphate, filtered, concentrated under vacuum and the residue is purified on a silica gel column (eluent:ethyl acetate). The pure fractions are collected and concentrated under vacuum. A white powder is obtained with a yield of 25%. The compound is then dissolved in methanol and salified by adding a 1N solution of HCl in ethyl ether (1 ml). After agitation for one hour at 20° C., the reaction mixture is concentrated under vacuum in order to produce a pale yellow powder. Melting point: the product turns into a foam.

NMR $^1$H (400 MHz, DMSO d6, δ): 3.71 (s, 2H, $CH_2$); 4.60 (broad s, 1H, NH); 6.75 (m, 1H, thiophene); 7.00 (m, 4H, arom.); 7.19 (m, 2H, arom.); 7.40 (m, 3H, arom.); 7.55 (m, 4H, arom.); 8.14 (m, 2H, thiophene); 8.95 (broad s, 1H, $NH^+$); 9.86 (broad s, 1H, $NH^+$); 10.41 (s, 1H, NH—CO); 11.60 (broad s, 1H, $NH^+$).

IR: $v_{C=O}$ (amide): 1649 $cm^{-1}$; $v_{C=N}$ (amidine): 1597 $cm^{-1}$.

Example 3

{4-{[2-thienyl(imino)methyl]amino}phenoxy}-N-[4-(phenylamino)phenyl]-acetamide hydroiodide: 3

3.1) tertiobutyl 4-nitrophenoxyacetate 3 g (21.6 mmol) of paranitrophenol, 8.94 g (64.8 mmol) of potassium carbonate and 8.42 g (43.2.mmol) of tertiobutyl bromoacetate are introduced under a nitrogen atmosphere, into a 250 ml flask containing 100 ml of THF. The reaction mixture is agitated at reflux for 2 hours. The solid is filtered and the filtrate is concentrated under reduced pressure. The residue is taken up in 50 ml of ethyl acetate and washed successively with 50 ml of water and 50 ml of salt water. The organic phase is dried over sodium sulphate, filtered and evaporated under vacuum. After purification of the pure fractions on a silica gel column (eluent:ethyl acetate/heptane 1:8) and concentration under vacuum, a white powder is obtained with yield of 50%. Melting point: 81–83° C.

NMR $^1$H (100 MHz, $CDCl_3$, δ): 1.50 (s, 9H, 3×$CH_3$); 4.60 (s, 2H, $CH_2$); 7.57 (AB, 4H, Ph-$NO_2$).

3.2) 4-nitrophenoxyacetic acid 2.58 g (10.2 mmol) of intermediate 3.1 is dissolved in 45 ml of dichloromethane in a 100 ml flask, under a nitrogen atmosphere. The mixture is cooled down to 0° C. and 7.85 ml (102 mmol) of trifluoroacetic acid is added dropwise. The reaction mixture is agitated for 3 and a half hours at ambient temperature. The solution is then concentrated under reduced pressure. The evaporation residue is taken up in 30 ml of ethyl acetate and washed with 20 ml of water. The organic phase is dried over sodium sulphate, filtered and concentrated under vacuum. A yellow solid is obtained with a yield of 89%. The product obtained is sufficiently pure to be used directly in the following stage. Melting point: 190–192° C.

NMR $^1$H (100 MHz, $CDCl_3$, δ): 2.00 (broad s, 1H, COOH); 4.80 (s, 2H, $CH_2$); 7.60 (AB, 4H, Ph-$NO_2$).

3.3) (4-nitrophenoxy)-N-[(4-phenylamino)phenyl] acetamide 1.65 g (8.98 mmol) of 4-aminodiphenylamine, 1.77 g (8.98 mmol) of intermediate 3.2 and 1.27 g (9.42 mmol) of hydroxybenzotriazole are dissolved in 40 ml of THF in a 100 ml flask, under a nitrogen atmosphere. When all have dissolved, 1.94 g (9.42 mmol) of 1,3-dicyclohexylcarbodi-imide is added and the reaction medium is left under agitation for 15 hours. The precipitate of dicyclohexylurea formed is filtered and rinsed with ethyl acetate. The filtrate is evaporated under vacuum and the evaporation residue is taken up in ethyl acetate, it then forms a precipitate which is filtered and rinsed using the same solvent. A greenish solid is obtained with a yield of 65%. The product obtained is sufficiently pure to be used directly in the following stage. Melting point: 192–195° C.

NMR $^1$H (100 MHz, $CDCl_3$, δ): 4.75 (s, 2H, $CH_2$—O); 5.70 (broad s, 1H, NH); 7.10 (m, 9H, arom.); 7.85 (AB, 4H, Ph-$NO_2$); 8.05 (broad s, 1H, NH—CO).

3.4) (4-aminophenoxy)-N-[(4-phenylamino)phenyl] acetamide 1 g (2.75 mmol) of intermediate 3.3 dissolved in 200 ml of a mixture of solvents (ethanol/dichloromethane/THF 1:1:1) and 0.1 g of Palladium on carbon at 10% are introduced into a 300 ml autoclave. The mixture is placed under a hydrogen pressure of 1.5 bar and agitated at ambient temperature for 15 minutes. The catalyst is filtered off and the solvents are concentrated under reduced pressure in order to produce a pinkish beige solid with a yield of 71%. Melting point: 146–148° C.

NMR $^1$H (100 MHz, $CDCl_3$, δ): 3.50 (broad s, 2H, $NH_2$); 4.50 (s, 2H, $CH_2$—O); 5.70 (broad s, 1H, NH); 6.70 (m, 4H, arom.); 7.10 (m, 4H, arom.); 7.25 (m, 5H, arom.); 8.20 (broad s, 1H, NH—CO).

3.5) [4-{[imino(2-thienyl)methyl]amino}phenoxy]-N-[(4-phenylamino)phenyl]acetamide hydroiodide: 3

A mixture of 0.3 g (0.9 mmol) of intermediate 3.4 in the presence of 0.25 g (0.9 mmol) of S-methyl-2-thiophene thiocarboximide hydroiodide in solution in 20 ml of isopropanol is heated at 50° C., for 15 hours. The reaction mixture is filtered and the solid obtained is rinsed with ethyl ether. A yellow powder is obtained with a yield of 78%. Melting point: 163–166° C.

NMR $^1$H (400 MHz, DMSO d6, δ): 4.75 (s, 2H, $CH_2O$); 6.77 (m, 1H, thiophene); 7.04 (m, 4H, arom.); 7.19 (m, 4H, arom.); 7.40 (m, 3H, arom.); 7.50 (m, 2H, arom.); 8.12 (m, 2H, thiophene); 8.81 (broad s, 1H, $NH^+$); 9.70 (broad s, 1H, $NH^+$); 10.01 (s, 1H, CO—NH); 11.20 (broad s, 1H, $NH^+$).

IR: $v_{C=O}$ (amide): 1647 $cm^{-1}$; $v_{C=N}$ (amidine): 1598 $cm^{-1}$.

Example 4

4-{[2-thienyl(imino)methyl]amino}-N-[2-(phenylamino)phenyl]-benzenebutanamide: 4

The experimental protocol used is the same as that described for Example 2. The product is obtained in the form of the free base (white solid). Melting point: 164–167° C.

NMR $^1$H (400 MHz, DMSO d6, δ): 1.86 (m, 2H, $CH_2$); 2.35 (m, 2H, $CH_2$); 2.55 (m, 2H, $CH_2$); 6.37 (broad s, 2H, $NH_2$); 6.76 (m, 3H, arom.); 6.87 (m, 2H, arom.); 6.96 (m, 1H, thiophene); 7.10 (m, 3H, arom.); 7.18 (m, 2H, arom.); 7.25 (m, 1H, arom.); 7.33 (s, 1H, NH); 7.52 (m, 1H, thiophene); 7.73 (m, 1H, thiophene); 9.36 (s, 1H, NH—CO).

IR: $v^{C=O}$ (amide): 1627 $cm^{-1}$; $v^{C=N}$ (amidine): 1591 $cm^{-1}$.

Example 5

4-{[2-thienyl(imino)methyl]amino}-N-[4-(phenylamino)phenyl]-benzenebutanamide hydrochloride: 5

The experimental protocol used is the same as that described for Example 2. The hydrochloride is obtained in the form of a salmon-pink powder. Melting point: 167–170° C.

NMR $^1$H (400 MHz, DMSO d6, δ): 1.90 (m, 2H, $CH_2$); 2.35 (m, 2H, $CH_2$); 2.70 (m, 2H, $CH_2$); 6.70 (m, 1H, thiophene); 7.00 (m, 4H, arom.); 7.20 (m, 2H, arom.); 7.40 (m, 5H, arom.); 7.50 (m, 2H, arom.); 8.20 (m, 2H, thiophene); 8.90 (s, 1H, $NH^+$); 9.85 (s, 1H, $NH^+$); 9.90 (s, 1H, NHCO); 11.55 (s, 1H, $NH^+$).

IR: $\nu_{C=O}$ (amide): 1654 $cm^{-1}$; $\nu_{C=N}$ (amidine): 1597 $cm^{-1}$.

Example 6

4-{[2-thienyl(imino)methyl]amino}-N-[4-(4-methoxyphenylamino)phenyl]-benzenebutanamide hydrochloride: 6

The experimental protocol used is the same as that described for intermediate 2.3, intermediate 6.2 replacing 4-amino-N-[4-(phenylamino)phenyl]-benzeneacetamide. A beige powder is obtained with a yield of 65%. Melting point: 200–202° C.

NMR $^1$H (400 MHz, DMSO d6, δ): 1.91 (m, 2H, $CH_2$); 2.33 (m, 2H, $CH_2$); 2.67 (m, 2H, $CH_2$); 3.69 (s, 3H, O—$CH_3$); 4.71 (broad s, 1H, NH); 6.81–7.00 (m, 6H, arom.); 7.37–7.45 (m, 7H, arom.); 8.20 (m, 2H, thiophene); 8.90 (broad s, 1H, $NH^+$); 9.87 (broad s, 1 H, $NH^+$); 9.92 (s, 1H, NH—CO); 11.67 (broad s, 1H, $NH^+$).

IR: $\nu_{C=O}$ (amide): 1664 $cm^{-1}$; $\nu_{C=N}$ (amidine): 1603 $cm^{-1}$.

Example 7

2-{4-{[2-thienyl(imino)methyl]amino}phenyl}-ethyl: [4-(phenylamino)phenyl]-carbamate hydrochloride: 7

7.1) 2-(4-nitrophenyl)-ethyl[4-(phenylamino)phenyl]-carbamate 1.18 g (3.9 mmol) of triphosgene is dissolved in 15 ml of dichloromethane in a 250 ml flask, under argon,. Using a motorized syringe, a solution of 2 g (12 mmol) of 4-nitrophenylethanol and 1.7 ml (13 mmol) of N,N-dimethylaniline in 40 ml of dichloromethane is added over 1 hour. The reaction mixture is agitated for a few minutes at 20° C. before adding in one go a solution of 2.2 g (12 mmol) of 4-aminodiphenylamine and 1.7 ml (13 mmol) of N,N-dimethylaniline in 40 ml of dichloromethane. After agitation for one hour at 20° C., the contents of the flask are poured into 100 ml of water. The mixture is diluted with 100 ml of dichloromethane and agitated. The organic phase is decanted, dried over magnesium sulphate, filtered and evaporated under vacuum. The solid obtained is taken up in ethyl ether, triturated and filtered. After drying, a greenish powder is obtained with a yield of 22%. Melting point: 146.4–148° C.

NMR $^1$H (400 MHz, $CDCl_3$, δ): 3.10 (m, 2H, $CH_2$); 4.40 (m, 2H, $CH_2$); 5.65 (s, 1H, NH); 6.50 (s, 1H, NH); 6.80–7.60 (m, 11H, arom.); 8.20 (m, 2H, arom.).

7.2) 2-(4-aminophenyl)-ethyl[4-(phenylamino)phenyl]-carbamate

The experimental protocol used is the same as that described for intermediate 2.2, intermediate 7.1 replacing 4-nitro-N-[4-(phenylamino)phenyl]-benzeneacetamide. A white solid is obtained with a yield of 48%. Melting point: 140–140.5° C.

NMR $^1$H (400 MHz, DMSO d6, δ): 2.75 (m, 2H, $CH_2$); 4.15 (m, 2H, $CH_2$); 5.20 (s, 2H, $NH_2$); 6.50 (m, 2H, arom.); 6.70 (m, 1H, arom.); 7.00 (m, 6H, arom.); 7.15 (m, 2H, arom.); 7.30 (m, 2H, arom.); 8.00 (s, 1H, NH); 9.40 (s, 1H, NH).

7.3) 2-{4-{[2-thienyl(imino)methyl]amino}phenyl}-ethyl[4-(phenylamino)phenyl]-carbamate hydrochloride: 7

The experimental protocol used is the same as that described for intermediate 2.3, intermediate 7.2 replacing 4-amino-N-[4-(phenylamino)phenyl]-benzeneacetamide. A white solid is obtained with a yield of 34%. Melting point: 153–159° C.

NMR $^1$H (400 MHz, DMSO d6, δ): 3.00 (m, 2H, $CH_2$); 4.30 (m, 2H, $CH_2$); 6.60–7.70 (m, 14H, arom.); 8.20 (m, 2H, thiophene); 8.90 (s, 1H, $NH^+$); 9.50 (s, 1H, NH—CO); 9.90 (s, 1H, $NH^+$); 11.70 (s, 1H, $NH^+$).

IR: $\nu_{C=O}$ (carbamate): 1719 $cm^{-1}$; $\nu_{C=N}$ (amidine): 1598 $cm^{-1}$.

Example 8

N-{2-{4-{[2-thienyl(imino)methyl]amino}phenyl}ethyl}-N'-[4-(phenylamino)phenyl]-urea hydrochloride: 8

8.1) N-[2-(4-nitrophenyl)-ethyl]-N'-[4-(phenylamino)phenyl]-urea 0.5 g (1.7 mmol) of triphosgene is dissolved in 8 ml of dichloromethane in a 100 ml flask, under argon. Using a motorized syringe, a solution of 0.92 g (5 mmol) of 4-aminodiphenylamine and 1.44 ml (8.2 mmol) of diisopropylethylamine in 15 ml of dichloromethane is added over one hour. Five minutes after the addition is finished, 1.01 g (5 mmol) of 4-nitrophenethylamine hydrochloride followed by a solution of 1.44 ml (8.2 mmol) of diisopropylethylamine in 10 ml of dichloromethane are added in a single portion. After agitation for two hours at 20° C., the reaction mixture is diluted with 50 ml of dichloromethane and 20 ml of water. The organic phase is decanted and rewashed with 20 ml of water. After drying over, $MgSO_4$ and filtration, the organic solution is partially concentrated under vacuum. The precipitate formed is collected by filtration and rinsed with dichloromethane. A yellow solid is obtained with a yield of 40%. Melting point: 204–205° C.

NMR $^1$H (100 MHz, DMSO d6, δ): 2.96 (m, 2H, $CH_2$); 3.50 (m, 2H, $\underline{CH_2}$—NH); 5.78 (m, 1H, $\underline{HN}$—$CH_2$); 6.45 (broad s, 1H, Ph-$\underline{NH}$—CO); 6.72–7.49 (m, 11H, arom.); 7.81 (broad s, 1H, NH); 8.15 (m, 2H, arom.).

8.2) N-[2-(4-aminophenyl)-ethyl]-N'-[4-(phenylamino)phenyl]-urea

A solution of intermediate 8.1 (0.68 g, 1.81 mmol) in 40 ml of a THF/ethanol mixture (3/1) as well as 0.1 g of Pd/C at 10% is introduced into a stainless steel autoclave equipped with a magnetic stirrer. The reaction mixture is agitated under hydrogen pressure (1.5 bar) for 1 hour at a temperature of 20° C. The Pd/C is then eliminated by filtration and the filtrate is concentrated under vacuum. The solid obtained is washed successively with ethyl acetate and dichloromethane. A beige powder is obtained with a yield of 61%. Melting point>260° C.

NMR $^1$H (100 MHz, DMSO d6, δ): 2.70 (m, 2H, CH$_2$); 3.40 (m, 2H, CH$_2$—NH); 5.18 (broad s, 2H, NH$_2$); 6.07 (m, 1H, HN—CH$_2$); 6.60–7.45 (m, 13H, arom.); 8.00 (broad s, 1H, NH); 8.41 (broad s, 1H, Ph-NH—CO).

8.3) N-{2-{4-{[2-thienyl(imino)methyl]amino}phenyl}ethyl}-N'-[4-(phenylamino)phenyl]-urea hydrochloride: 8

0.38 g (1.10 mmol) of intermediate 8.2 and 0.34 g (1.21 mmol) of S-methyl-2-thiophene thiocarboximide hydroiodide are dissolved in 20 ml of isopropanol in a 50 ml flask. The reaction mixture is agitated for 20 hours at a temperature of 60° C. After evaporation of the solvent under vacuum, the residue is taken up in 50 ml of a 1/1 mixture of a saturated solution of Na$_2$CO$_3$ and ethyl acetate. The reaction medium is vigorously agitated and after a few moments a precipitate appears. This is collected, filtered and rinsed successively with ethyl acetate and water. After drying, the precipitate is purified on a silica gel column (eluent THF). The pure fractions are collected and concentrated under vacuum. The solid obtained (300 mg) is redissolved in 80 ml of THF to which 2 ml of a 1N solution of HCl in ethyl ether is added. The hydrochloride formed precipitates, it is filtered and rinsed with THF followed by ethyl ether in order to produce a light grey powder. Melting point: the product becomes a foam.

NMR $^1$H (400 MHz, DMSO d6, δ): 2.80 (m, 2H, CH$_2$); 3.37 (m, 2H, CH$_2$); 4.46 (broad s, 1H, NH); 6.40 (broad s, 1H, NH-CH$_2$); 6.70 (m, 1H, thiophene); 6.94 (m, 4H, arom.); 7.15 (m, 2H, arom.); 7.28 (m, 2H, arom.); 7.40 (m, 5H, arom.); 8.17 (m, 2H, thiophene); 8.78 (broad s, 1H, Ph-NH—CO); 8.93 (board s, 1H, NH$^+$); 9.84 (broad s, 1H, NH$^+$); 11.52 (broad s, 1H, NH$^+$).

IR: $ν_{C=O}$ (urea): 1654 cm$^{-1}$; $ν_{C=N}$ (amidine): 1598 cm$^{-1}$.

Example 9

4-{4-{[2-thienyl(imino)methyl]amino}phenyl}-N-[4-(phenylamino)phenyl]-1-piperazine acetamide hydrochloride: 9

9.1) ethyl 4-(nitrophenyl)-1-piperazine acetate 3 g (14.5 mmol) of 1-(4-nitrophenylpiperazine) and 1.8 ml (15.9 mmol) of bromoethyl acetate are dissolved in 60 ml of dichloromethane in a 100 ml flask. After the addition of 2.42 ml (17.4 mmol) of triethylamine, the reaction mixture is agitated, at 20° C., for one hour. The solution is then poured into 100 ml of water and extracted with 100 ml of dichloromethane. After decantation, the organic phase is dried over magnesium sulphate, filtered and concentrated under vacuum. The solid obtained is taken up in ethyl ether, triturated and filtered. A yellow powder is obtained with a yield of 89%. Melting point: 122.1–122.5° C.

NMR $^1$H (400 MHz, CDCl$_3$, δ): 1.3 (t, 3H, CH$_3$, J=7 Hz); 2.75 (m, 4H, piperazine); 3.30 (s, 2H, CO—CH$_2$); 3.50 (m, 4H, piperazine); 4.20 (q, 2H, CH$_2$—CH$_3$, J=7 Hz); 7.45 (AB, 4H, Ph-NO$_2$).

9.2) 4-(nitrophenyl)-1-piperazine acetic acid 32.4 ml of a 1M aqueous solution of LiOH is added dropwise at 20° C. into a flask containing a solution of 3.8 g (13 mmol) of intermediate 9.1 in solution in 80 ml of THF. After agitation for one hour, the reaction mixture is acidified to pH=5 with a 2N solution of hydrochloric acid. The precipitate obtained is filtered and rinsed with a minimum amount of THF and water. The product is used as it is in the following stage.

NMR $^1$H (100 MHz, D$_2$O, δ): 3.30 (m, 4H, piperazine); 3.60 (m, 6H, piperazine+CO—CH$_2$); 7.45 (AB, 4H, Ph-NO$_2$).

9.3) 4-(4-nitrophenyl)-N-[4-(phenylamino)phenyl]-1-piperazine acetamide

The protocol used is the same as that described for intermediate 2.1, intermediate 9.2 replacing 4-nitrophenylacetic acid. A yellow solid is obtained with a yield of 84%. Melting point: 212–213° C.

NMR $^1$H (400 MHz, CDCl$_3$, δ): 2.80 (m, 4H, piperazine); 3.25 (s, 2H, CO—CH$_2$); 3.50 (m, 4H, piperazine); 5.70 (s, 1H, NH); 6.90 (m, 3H, arom.); 7.10 (m, 4H, arom.); 7.30 (m, 2H, arom.); 7.85 (AB, 4H, Ph-NO$_2$); 8.90 (s, 1H, NHCO).

9.4) 4-(4-aminophenyl)-N-[4-(phenylamino)phenyl]-1-piperazine acetamide

The protocol used is the same as that described for intermediate 2.2, intermediate 9.3 replacing 4-nitro-N-[4-(phenylamino)phenyl]-benzeneacetamide. A brown oil is obtained with a yield of 71%.

NMR $^1$H (400 MHz, CDCl$_3$, δ): 2.80 (m, 4H, piperazine); 3.15 (m, 4H, piperazine); 3.15 (m, 4H, piperazine); 3.20 (s, 2H, CO—CH$_2$); 5.70 (s, 1H, NH); 6.70 (m, 2H, arom.); 6.90 (m, 3H, arom.); 7.10 (m, 4H, arom.); 7.30 (m, 2H, arom.); 7.50 (m, 2H, arom.); 9.10 (s, 1H, NHCO).

9.5) 4-{4-{[2-thienyl(imino)methyl]aminol}phenyl}-N-[4-(phenylamino)phenyl]-1-piperazine acetamide hydrochloride: 9

The protocol used is the same as that described for intermediate 2.3, intermediate 9.4 replacing 4-amino-N-[4-(phenylamino)phenyl]-benzeneacetamide. A yellow solid is obtained with a yield of 30%. Melting point: 230–240° C.

NMR $^1$H (400 MHz, DMSO d6, δ): 3.10–3.50 (m, 4H, piperazine); 3.65 (m, 2H, piperazine); 3.90 (m, 2H, piperazine); 4.30 (s, 2H, CO—CH$_2$); 6.80 (m, 1H, thiophene); 6.90–7.40 (m, 11H, arom.); 7.50 (m, 2H, arom.); 8.15 (m, 2H, thiophene); 8.75 (s, 1H, NH$^+$); 9.80 (s, 1H, NH$^+$); 10.9 (m, 2H, NHCO+NH$^+$); 11.40 (s, 1H, NH+).

IR: $ν_{C=O}$ (amide): 1680 cm$^{-1}$; $ν_{C=N}$ (amidine): 1512 cm$^{-1}$.

Example 10

1-{[(4-phenylamino)phenylamino]carbonyl}-4-{4-{[2-thienyl(imino)methyl]amino}phenyl}-piperazine hydrochloride: 10

The experimental protocol used is the same as that described for Example 8. The product is salified under conditions which are identical to compound 2 except that THF replaces methanol. A yellow powder is obtained. Melting point: 239–240° C.

NMR $^1$H (400 MHz, DMSO d6, δ): 3.30 (broad s, 4H, piperazine); 3.70 (broad s, 4H, piperazine); 5.80 (broad s, 1H, NH); 6.73 (m, 1H, thiophene); 6.98 (m, 4H, arom.); 7.17 (m, 2H, arom.); 7.28–7.37 (m, 7H, arom.); 8.16 (m, 2H, thiophene); 8.65 (broad s, 1H, Ph-NH—CO); 8.80 (broad s, 1H, NH$^+$); 9.80 (broad s, 1H, NH$^+$); 11.52 (broad s, 1H, NH$^+$).

IR: $\nu_{C=O}$ (urea): 1654 cm$^{-1}$; $\nu_{C=N}$ (amidine): 1597 cm$^{-1}$.

Example 11

4-{[2-thienyl(imino)methyl]amino}-N-[4-(phenylamino)phenyl]-benzenebutanamine hydrochloride: 11

11.1) 4-Nitro-N-[4-(phenylamino)phenyl]-benzenebutanamine 1.12 g (3 mmol) of 4-nitro-N-[4-(phenylamino)phenyl]-benzenebutanamide (obtained under the same conditions as intermediate 2.1) is dissolved in 50 ml of anhydrous THF in a 250 ml three-necked flask under an argon atmosphere. The solution is cooled down using an ice bath, before the dropwise addition of 15 ml (15 mmol) of a solution of diborane/THF. The reaction mixture is heated to reflux for 5 hours. After returning the temperature to 20° C., 25 ml of an HCl solution (6N) is added slowly dropwise and the mixture is taken to reflux for 2 hours. The solution is then cooled down using an ice bath before the addition of a 20% soda solution until a basic pH is reached. The product is extracted using ethyl ether (2×50 ml), the organic solution is washed with salt water (2×50 ml) and dried over magnesium sulphate. After filtration and concentration under vacuum, the residue is purified on a silica gel column (eluent:heptane/AcOEt 1/1). The pure fractions are collected and evaporated under vacuum in order to produce a brown oil with a yield of 28%.

NMR $^1$H (400 MHz, DMSO d6,δ): 1.55 (m, 2H, CH$_2$); 1.71 (m, 2H, CH$_2$); 2.75 (m, 2H, CH$_2$-Arom); 2.98 (m, 2H, HN—CH$_2$); 5.29 (m, 1H, NH); 6.51–7.51 (m, 12H, Arom.+NH); 8.15 (m, 2H, Ph-NO$_2$).

11.2) 4-Amino-N-[4-(phenylamino)phenyl]-benzenebutanamine

The experimental protocol used is the same as that described for intermediate 2.2, intermediate 11.1 replacing 4-nitro-N-[4-(phenylamino)phenyl]-benzeneacetamide. A brown oil is obtained with a yield of 36%.

NMR $^1$H (400 MHz, DMSO d6, δ): 1.55 (m, 4H, 2×CH$_2$); 2.44 (m, 2H, CH$_2$); 2.97 (m, 2H, CH$_2$); 4.81 (s, 2H, NH$_2$); 5.27 (m, 1H, NH); 6.47–7.10 (m, 13H, arom.); 7.49 (s, 1H, NH).

11.3) 4-{[2-thienyl(imino)methyl]amino}-N-[4-(phenylamino)phenyl]-benzenebutanamine hydrochloride: 11

0.10 g (0.3 mmol) of intermediate 11.2 and 0.11 g (0.37 mmol) of S-methyl-2-thiophene thiocarboximide hydroiodide are dissolved in 5 ml of isopropanol with 0.05 ml (0.6 mmol) of pyridine added to it, in a 50 ml flask. The reaction mixture is agitated for 20 hours at a temperature of 23° C. After evaporation of the solvent under vacuum, the residue is taken up in 25 ml of a mixture (1/1) of a saturated solution of NaHCO$_3$ and dichloromethane. After decantation, the organic phase is washed with 2×25 ml of salt water. The organic solution is dried over magnesium sulphate, filtered, concentrated under vacuum and the residue is purified on a silica gel column (eluent:dichloromethane+5% of ethanol). The pure fractions are collected and concentrated under vacuum. A pinkish powder is obtained which is salified by adding a 1N solution of HCl in ethyl ether (1 ml) to the solution of the base in acetone. After agitation for one hour at 20° C., the reaction mixture is filtered and the powder is washed successively with 20 ml of acetone and 20 ml of ethyl ether. Melting point: 165–166 ° C.

NMR $^1$H (400 MHz, DMSO d6, δ): 1.71 (m, 4H, 2×CH$_2$); 2.66 (m, 2H, CH$_2$); 3.20 (m, 2H, CH$_2$); 6.85–7.41 (m, 14H, arom.); 8.16 (m, 2H, thiophene); 8.53 (broad s, 1H, NH); 8.87 (broad s, 1H, NH$^+$); 9.83 (broad s, 1H, NH+); 11.19 (broad s, 2H, 2×NH$^+$); 11.56 (broad s, 1H, NH$^+$).

IR: $\nu_{C=N}$ (amidine): 1595 cm$^{-1}$.

Example 12

3-{[2-thienyl(imino)methyl]amino}-N-[4-(phenylamino)phenyl]-benzenepropanamide hydrochloride: 12

12.1) 3-nitrophenylethanol mesylate

A solution of 4.63 ml (59.8 mmol) of methane sulphonyl chloride diluted with 20 ml of dichloromethane is added dropwise to a solution of 10 g (59.8 mmol) of 3-nitrophenylethanol and 8.31 ml (59.8 mmol) of triethylamine in 120 ml of dichloromethane, cooled down with an ice bath. Agitation is maintained for 1 hour at 0° C. and for 2 hours at 20° C. The reaction mixture is then concentrated under vacuum and the residue is taken up in 125 ml of ethyl acetate and 100 ml of water. After agitation and decantation, the organic phase is washed successively with 100 ml of water and 100 ml of salt water. The organic solution is dried over magnesium sulphate, filtered and concentrated under vacuum. The evaporation residue is purified on a silica column (eluent heptane/ethyl acetate 6/4) and the pure fractions are collected and evaporated in order to produce a yellow oil with a yield of 71%.

NMR $^1$H (100 MHz, CDCl$_3$, δ): 3.00 (s, 3H, CH$_3$); 3.20 (t, 2H, CH$_2$, J=5.8 Hz); 4.50 (t, 2H, CH$_2$); 7.60 (m, 2H, arom.); 8.20 (m, 2H, arom.).

12.2) 3-nitrobenzene-propanenitrile 0.49 g (10 mmol) of NaCN is introduced in one portion into a 100 ml flask ml, under an argon atmosphere, containing a solution of 1.22 g (5 mmol) of intermediate 12.1 in 20 ml of dry DMF. The reaction mixture is heated at 60° C. for 3 hours and, after allowing the temperature to return to 20° C., poured into 100 ml of water. The solution is extracted with 5×50 ml of ethyl acetate, the organic phases are collected and washed successively with 100 ml of water and 100 ml of salt water. After drying over magnesium sulphate, the organic solution is concentrated under vacuum and the residue is purified on a silica column (eluent:heptane/ethyl acetate: 7/3). The pure fractions are collected and concentrated under vacuum in order to produce a light yellow powder with a yield of 78%. Melting point: 86–88° C.

NMR $^1$H (100 MHz, CDCl$_3$, δ): 2.70 (t, 2H, CH$_2$, J=5.8 Hz); 3.10 (t, 2H, CH$_2$); 7.60 (m, 2H, arom.); 8.20 (m, 2H, arom.).

12.3) 3-nitrobenzene propanoic acid

A solution of 2.33 g (19.2 mmol) of intermediate 12.2 in 100 ml of a 10% aqueous solution of HCl and 100 ml of ethanol is taken to reflux for 72 hours. After allowing the temperature to return to 20° C., the reaction mixture is concentrated to dryness under vacuum. The residue is taken up in 100 ml of ethyl acetate and washed with 3×100 ml of water and with 50 ml of salt water. After drying over sodium sulphate, the organic solution is filtered and concentrated under vacuum. The evaporation residue is purified on a silica column (eluent:heptane/ethyl acetate 95/5 up to 80/20). A light yellow powder is obtained with a yield of 21%. Melting point: 107–109° C.

NMR $^1$H (100 MHz, CDCl$_3$, δ): 2.70 (m, 2H, CH$_2$); 3.10 (m, 2H, CH$_2$); 5.40 (broad s, 1H, 7.50 (m, 2H, arom.); 8.10 (m, 2H, arom.).

12.4) 3-nitro-N-[4-(phenylamino)phenyl]-benzenepropanamide

The experimental protocol used is the same as that described for intermediate 2.1, intermediate 12.3 replacing 4-nitrophenylacetic acid. A brown powder is obtained with a yield of 70%. Melting point: 130–132° C.

NMR $^1$H (CDCl$_3$, 100 MHz, δ): 2.70 (t, 2H, CH$_2$, J=5.8 Hz); 3.20 (t, 2H, CH$_2$); 5.70 (broad s, 1H, NH); 6.90–7.60 (m, 13H, arom.).

12.5) 3-amino-N-[4-(phenylamino)phenyl]-benzenepropanamide

The experimental protocol used is the same as that described for intermediate 2.2, intermediate 12.4 replacing 4-nitro-N-[4-(phenylamino)phenyl]-benzeneacetamide. A white powder is obtained with a yield of 64%. Melting point: 164–166° C.

NMR $^1$H (CDCl$_3$, 100 MHz, δ): 2.80 (m, 2H, CH$_2$); 3.50 (m, 2H, CH$_2$); 5.10 (broad s, 2H, NH$_2$); 6.50 (m, 3H, arom.); 6.80–7.45 (m, 8H, arom.); 7.60 (m, 2H, arom.); 8.15 (s, 1H, NH); 9.88 (s, 1H, NH—CO).

12.6) 3-{[2-thienyl(imino)methyl]amino}-N-[4-(phenylamino)phenyl]-benzenepropanamide hydrochloride: 12

The experimental protocol used is the same as that described for intermediate 2.3, intermediate 12.5 replacing 4-amino-N-[4-(phenylamino)phenyl]-benzeneacetamide. After salification, a light beige powder is obtained with a yield of 78%. Melting point: 228–230° C.

NMR $^1$H (400 MHz, DMSO d6, δ): 2.70 (m, 2H, CH$_2$); 2.96 (m, 2H, CH$_2$); 5.20 (broad s, 1H, NH); 6.74 (m, 1H, thiophene); 7.00 (m, 4H, arom.); 7.19 (m, 2H, arom.); 7.29 (m, 1H, arom.); 7.39 (m, 3H, arom.); 7.47 (m, 3H, arom.); 8.18 (m, 2H, thiophene); 8.96 (broad s, 1H, NH$^+$); 9.90 (broad s, 1H, NH$^+$); 10.07 (s, 1H, NH—CO); 11.60 (broad s, 1H, NH$^+$).

IR: $\nu_{C=O}$ (amide): 1649 cm$^{-1}$; $\nu_{C=N}$ (amidine): 1596 cm$^{-1}$.

Example 13

4-(4-{[amino(2-thienyl)methylidene]amino}phenyl)-N-[2-(4-toluidino)phenyl]butanamide: 13

13.1) N'-(4-methylphenyl)-1,2-benzenediamine

The reduction of the nitro function of N-(4-methylphenyl)-2-nitroaniline (*Synthesis* (1990) 430) is carried out in the presence of Pd/C in ethanol, under the conditions described previously for intermediate 2.2. A violet product is obtained in a semi-oil semi-crystal form with a yield of 90%.

13.2) 4-(4-{[amino(2-thienyl)methylidene]amino}phenyl)-N-[2-(4-toluidino)phenyl]butanamide The experimental protocol used is the same as that described for Example 2, starting from 4-nitrophenylbutyric acid and intermediate 13.1. The product is isolated in the form of a free base. White solid. Melting point: 66–68° C.

Example 14

4-anilinophenyl-4-(4-{[amino(2-thienyl)methylidene]amino}-phenyl)butanoate: 14

14.1) 4-anilinophenyl 4-(4-nitrophenyl)butanoate 0.98 g (6.02 mmol) of 1,1'-carbonyldiimidazole is slowly added at 20° C. to a solution of 1.25 g (5.96 mmol) of 4-nitrophenylbutyric acid in 25 ml CH$_2$Cl$_2$. The reaction mixture is agitated for 30 minutes before the addition of 1 g (5.42 mmol) of 4-hydroxy-diphenylamine. After agitation for 3 hours, the reaction is stopped by the addition of 3 ml of MeOH and the solvent is evaporated under vacuum. The evaporation residue is purified on a silica column (eluent: Heptane/AcOEt: 100/0 to 80/20). A yellow solid is obtained with a yield of 89%.

14.2) 4-anilinophenyl 4-(4-{[amino(2-thienyl)methylidene]amino}phenyl)butanoate The experimental protocol used is the same as that described for intermediates 2.2 and 2.3, starting from intermediate 14.1. The product is isolated in the form of a free base. Pale yellow solid. Melting point: 147–148° C.

Example 15

4-(4-{[amino(2-thienyl)methylidene]amino}phenyl)-N-[2-(4-toluidino)phenyl]butanamide: 15

15.1) N-{4-[4-(4-nitrophenyl)butoxy]phenyl}-N-phenylamine 2.0 g (10.88 mmol) of 4-hydroxy-diphenylamine, 2.0 ml (12 mmol) of 4-(4-nitrophenyl)-1-butanol and 1.66 ml (12 mmol) of tributylphosphine are successively introduced into a flask containing 10 ml CH$_2$Cl$_2$. 1.90 ml (12 mmol) of diethylazodicarboxylate is then added dropwise and the whole is agitated at 20° C. for 16 hours. The solvent is evaporated off under vacuum and the residue is purified on a silica column (eluent:heptane/AcOEt: 100/0 to 80/20). The expected product is obtained in the form of a dark red oil with a yield of 35%.

15.2) N'-{4-[4-(4-anilinophenoxy)butyl]phenyl}-2-thiophenecarboximidamide

The experimental protocol used is the same as that described for intermediates 2.2 and 2.3, starting from intermediate 14.1. The product is isolated in the form of a free base. White solid. Melting point: 120–121° C.

Example 16

N'-{4-[4-(3-anilinophenoxy)butyl]phenyl}-2-thiophenecarboximidamide: 16

The experimental protocol used is the same as that described for Example 15, starting from 3-hydroxy-diphenylamine. The product is isolated in the form of a free base. White solid. Melting point: 73–74° C.

Example 17

N'-(9H-carbazol-3-yl)-2-thiophenecarboximidamide: 17

The experimental protocol used is the same as that described for Example 1, starting from 3-aminocarbazole (*Pharmazie* (1993) 48(11), 817–820). The product is isolated in the form of a free base. Light beige solid. Melting point: 243–244° C.

Example 18

4-(4-{[amino(2-thienyl)methylidene]amino}phenyl)-N-(9H-carbazol-3-yl)butanamide hydrochloride: 18

The experimental protocol used is the same as that described for Example 2, starting from 3-aminocarbazole (*Pharmazie* (1993) 48(11), 817–820) and 4-nitrophenylbutyric acid. Light beige solid. Melting point>250° C.
MS: MH$^+$: 452.2.

Example 19

N'-[4-(10H-phenothiazin-2-yloxy)phenyl]-2-thiophenecarboximidamide hydroiodide: 19

19.1) 2-(4-nitrophenoxy)-10H-phenothiazine 1.1 g (5.11 mmol) of 2-hydroxy-10H-phenothiazine (*J. Med. Chem.* (1992) 35, 716), 1.34 g (9.71 mmol) of K$_2$CO$_3$ and 0.94 g (6.64 mmol) of 4-fluoro-1-nitrobenzene are mixed in 25 ml anhydrous DMF in a flask under argon atmosphere,. The reaction mixture is heated at 70° C. for 18 hours. The solvent is then evaporated off under vacuum and the residue is taken up in 50 ml of AcOEt and 50 ml of water. After agitation and decantation, the organic phase is washed with 50 ml of salt water. The organic solution is dried over MgSO$_4$, filtered and concentrated under vacuum. The residue is crystallized from diisopropyl ether. After drying, a yellow solid is obtained with a yield of 83%. Melting point: 210–211° C.

19.2) N'-[4-(10H-phenothiazin-2-yloxy)phenyl]-2-thiophenecarboximidamide hydroiodide The experimental protocol used is the same as that described for intermediates 2.2 and 2.3, starting from intermediate 19.1. The expected final product precipitates directly from the reaction mixture, it is isolated by filtration and washed using iPrOH. Yellow solid. Melting point: 175–180° C.

Example 20

N'-{4-[(10-methyl-10H-phénothiazin-2-yl)oxy]phenyl}-2-thiophenecarboximidamide hydrochloride: 20

20.1) 10-methyl-10H-phenothiazin-2-yl4-nitrophenylether 0.014 g (0.58 mmol) of NaH (60%) is added to a flask under argon atmosphere, containing a solution of 0.1 g (0.29 mmol) of intermediate 19.1 in 10 ml of anhydrous DMF. Agitation is maintained, at 20° C., for 16 hours. 0.04 ml (0.58 mmol) of MeI is then added to the reaction mixture, under agitation at 20° C. At the end of the reaction, the whole is poured into 50 ml of ice-cooled water and the product is extracted using 50 ml of AcOEt. The organic phase is decanted, washed with 50 ml of salt water, dried over MgSO$_4$, filtered and concentrated under vacuum. The residue is purified on a silica column (eluent:heptane/AcOEt: 80/20). An orange oil is obtained with a yield of 50%.

20.2) N'-{4-[(10-methyl-10H-phenothiazin-2-yl)oxy]phenyl}-2-thiophenecarboximidamide hydrochloride The experimental protocol used is the same as that described for intermediates 2.2 and 2.3, starting from intermediate 20.1. A white solid is obtained. Melting point: 256–257° C.

Example 21

4-(4-{[amino(2-thienyl)methylidene]amino}phenyl)-N-(10H-phenothiazin-3-yl)butanamide hydrochloride: 21

21.1) 3-amino-10H-phenothiazine

Reduction of the nitro function of 3-nitro-10H-phenothiazine (*J. Org. Chem.* (1972) 37, 2691) is carried out in the presence of Pd/C in an EtOH/THF mixture under the conditions described for intermediate 2.2. A grey solid is obtained with a yield of 97%. Melting point: 150–156° C.

21.2) 4-(4-{[amino(2-thienyl)methylidene]amino}phenyl)-N-(10H-phenothiazin-3-yl)butanamide hydrochloride The experimental protocol used is the same as that described for Example 2, starting from 4-nitrophenylbutyric acid and intermediate 21.1. Light green solid. Melting point: 170–176° C.

Example 22

N'-(4-{4-[2-(10H-phenothiazin-2-yloxy)ethyl]-1-piperazinyl}phenyl)-2-thiophenecarboximidamide dihydrochloride: 22

22.1) 2-[4-(4-nitrophenyl)-1-piperazinyl]-1-ethanol 7.5 g (60 mmol) of 2-bromoethanol is added, under argon atmosphere, to a mixture of 10.35 g (50 mmol) of 1-(4-nitrophenyl)piperazine, 7.6 g (55 mmol) of K$_2$CO$_3$ and 9 ml (65 mmol) of Et$_3$N in 200 ml of CH$_2$Cl$_2$. The whole is then heated at 45° C. for 18 hours. The reaction mixture is finally diluted with 50 ml water, agitated and decanted. The organic phase is washed with 50 ml of salt water, dried over MgSO$_4$, filtered and concentrated under vacuum. The residue is crystallized from diisopropyl ether. A yellow solid is obtained with a yield of 89%. Melting point: 98–99° C.

22.2) 1-(2-bromoethyl)-4-(4-nitrophenyl)piperazine 8.6 g (26 mmol) of CBr$_4$ is added to a solution of 5 g (20 mmol) of intermediate 22.1 in 75 ml of CH$_2$Cl$_2$. The whole is cooled using an ice bath before the addition, by portions, of 6.3 g (24 mmol) of triphenylphosphine. Agitation is maintained for 2 hours at 20° C. After the addition of 50 ml of water, agitation and decantation, the organic phase is washed with 50 ml of salt water, dried over MgSO$_4$, filtered and concentrated under vacuum. The evaporation residue is purified on a silica column (eluent:CH$_2$Cl$_2$/EtOH: 95/5) and finally crystallized from ethyl ether. A yellow-orange solid is obtained with a yield of 40%. Melting point: 134–135° C.

22.3) 2-{2-[4-(4-nitrophenyl)-1-piperazinyl]ethoxy}-10H-phenothiazine

The experimental protocol used is the same as that described for intermediate 19.1, starting from intermediate 22.2. A yellow solid is obtained with a yield of 43%. Melting point: 224–225° C.

22.4) N'-(4-{4-[2-(10H-phenothiazin-2-yloxy)ethyl]-1-piperazinyl}-phenyl)-2-thiophenecarboximidamide dihydrochloride The experimental protocol used is the same as that described for intermediates 2.2 and 2.3 starting from intermediate 22.3. Light beige solid. Melting point: 198–200° C.

Example 23

4-(4-{[amino(2-thienyl)methylidène]amino}phenyl)-N-[4-(4-toluidino)phenyl]butanamide hydrochloride: 23

23.1) N'-(4-methylphenyl)-1,4-benzenediamine

Reduction of the nitro function of N-(4-methylphenyl)-4-nitroaniline (*Indian J. Chem.* (1981) 20B, 611–613) is carried out in the presence of Pd/C in ethanol, under the conditions described for intermediate 2.2. A grey solid is obtained with a yield of 85%.

23.2) 4-(4-{[amino(2-thienyl)methylidene]amino}phenyl)-N-[4-(4-toluidino)phenyl]butanamide hydrochloride The experimental protocol used is the same as that described for Example 2, starting from intermediate 22.3 and 4-nitrophenylbutynic acid. Yellow solid. Melting point: 142–145° C.

Example 24

3-anilinophenyl4-(4-{[amino(2-thienyl)methylidene]amino}-phenyl)butanoate: 24

The experimental protocol used is the same as that described for Example 14, starting from 3-hydroxy-diphenylamine and 4-nitrophenylbutyric acid. White solid. Melting point: 110–112° C.

Example 25

2-(4-{[amino(2-thienyl)methylidene]amino}phenyl)-N-[2-(9H-carbazol-4-yloxy)ethyl]acetamide hydrochloride: 25

25.1) 3-(2-bromoethoxy)-9H-carbazole

A mixture of 1.83 g (10 mmol) of 4-hydroxcarbazole (*J. Chem. Soc.* (1955), 3475–3477; *J. Med. Chem.* (1964) 7, 158–161), 1.08 ml (12.5 mmol) of 1,2-dibromoethane and 2.6 ml (10.5 mmol) of a 4 M aqueous solution of NaOH in 2 ml of water is heated under reflux for 5 hours. After the temperature returns to 20° C., the product is extracted using 2 times 30 ml of CH$_2$Cl$_2$. The organic solutions collected are then successively washed with 20 ml of water and 20 ml of salt water. After drying over MgSO$_4$, filtration and concentration under vacuum, the residue is purified on a silica column (eluent:heptane/AcOEt: 80/20). A beige powder is obtained with a yield of 32%. Melting point: 135–136° C.

25.2) 3-(2-azidoethoxy)-9H-carbazole

A mixture of 0.9 g (3.1 mmol) of intermediate 25.1 and 0.20 g (3.1 mmol) of NaN$_3$ in 10 ml of DMF is heated at 70° C. for 1 hour. The whole is then poured into 30 ml of a mixture of water and ice. After the addition of 50 ml of AcOEt and agitation, the organic phase is decanted and washed successively with 20 ml of water and 20 ml of salt water. The organic solution is then dried over Na$_2$SO$_4$, filtered and concentrated under vacuum. After drying, a beige powder is obtained (quantitative yield) which is used as is in the following stage.

25.3) 2-(9H-carbazol-3-yloxy)ethylamine

A solution of intermediate 25.2 in 50 ml EtOH as well as 0.3 g Pd/C (10%) are introduced into a stainless steel autoclave equipped with a magnetic stirrer. The reaction mixture is agitated for 2 hours under 1.5 bar H$_2$ at a temperature of 25° C. The Pd/C is then eliminated by filtration and the filtrate is concentrated under vacuum until dryness. The residue is taken up in ethyl ether and the crystals formed are filtered and abundantly rinsed with ethyl ether. After drying, a white powder is obtained with a yield of 82%. Melting point: 145–146° C.

25.4) 2-(4-{[amino(2-thienyl)methylidene]amino}phenyl)-N-[2-(9H-carbazol-4-yloxy)ethyl]acetamide hydrochloride The experimental protocol used is the same as that described for Example 2, starting from intermediate 25.3 and 4-nitrophenylbutyric acid. Light beige solid. Melting point: 233–234° C.

Example 26

N-(4-{[amino(2-thienyl)methylidene]amino}phenethyl)-2-anilinobenzamide hydrochloride: 26

The experimental protocol used is the same as that described for Example 2, starting from N-phenylanthranilic acid and 4-nitrophenethalamine. Pale yellow solid. Melting point: 163–165° C.

Example 27

N-(4-{[amino(2-thienyl)methylidene]amino}phenethyl)-2-(2,3-dimethylanilino)benzamide hydrochloride: 27

The experimental protocol used is the same as that described for Example 2, starting from mefenamic acid and 4-nitrophenethylamine. Pale yellow solid. Melting point: 168–170° C.

Example 28

N'-{4-[4-(2-anilinobenzoyl)-1-piperazinyl]phenyl}-2-thiophenecarboximidamide dihydrochloride: 28

The experimental protocol used is the same as that described for Example 2, starting from N-phenylanthranilic acid and 4-nitrophenylpiperazine. Pale yellow solid. Melting point: 168–170° C.

Example 29

N'-(4-{4-[2-(2,3-dimethylanilino)benzoyl]-1-piperazinyl}phenyl)-2-thiophenecarboximidamide dihydrochloride: 29

The experimental protocol used is the same as that described for Example 2, starting from mefenamic acid and 4-nitrophenylpiperazine. Pale yellow solid. Melting point: 166–168° C.

Example 30

4-(4-{[amino(2-thienyl)methylidene]amino}phenyl)-N-(4-phenoxyphenyl)butanamide hydrochloride: 30

The experimental protocol used is the same as that described for Example 14, starting from 4-nitrophenylbutyric acid and 4-phenoxyphenol. Pale yellow solid. Melting point: 119–123° C.

Example 31

N-(4-{[amino(2-thienyl)methylidene]amino}phénethyl)-4-(4-hydroxyphénoxy)benzamide hydrochloride: 31

The experimental protocol used is the same as that described for Example 2, starting from 4-(4-hydroxyphenoxy)benzoic acid and 4-nitrophenethylamine. Pale yellow solid. Melting point: 155–157° C.

Example 32

N-[2-(9H-carbazol-4-yloxy)ethyl]-2-thiophenecarboximidamide: 32

The experimental protocol used is the same as that described for intermediate 2.3, starting from intermediate 25.3. The expected product is isolated in the form of a free base. White solid. Melting point: 180–181° C.

Example 33

N-[3-(9H-carbazol-4-yloxy)propyl]-2-thiophenecarboximidamide: 33

33.1) 2-[3-(9H-carbazol-4-yloxy)propyl]-1H-isoindole-1,3(2H)dione 1 g (5.46 mmol) of 4-hydroxycarbazole (J. Chem. Soc. (1955), 3475–3477; J. Med. Chem. (1964) 7, 158–161) is added to a suspension, under argon, of 0.23 g (5.73 mmol) of NaH (60%) in 20 ml anhydrous DMF. After agitation for 30 minutes at 20° C., 1.46 g (5.46 mmol) of 3-bromopropylphtalimide in solution in 10 ml of anhydrous DMF is added dropwise to the reaction mixture. The whole is heated at 80° C. for 16 hours. After the temperature returns to 20° C., 5 ml of water is added and the mixture is concentrated under vacuum. The residue is taken up in 300 ml of $CH_2Cl_2$ and the organic solution is washed successively with 50 ml of 1M NaOH, 100 ml of water and 100 ml of salt water. After drying over $MgSO_4$, filtration and concentration under vacuum, an oily residue is obtained which slowly crystallizes. The crystals are washed using ethyl ether. A beige solid is obtained with a yield of 40%. Melting point: 171–172° C.

33.2) 3-(9H-carbazol-4-yloxy)propylamine

A solution of 0.13 ml (3.24 mmol) hydrazine hydrate in 5 ml ethanol is added dropwise to a solution of 0.8 g (2.16 mmol) of intermediate 33.1 in 30 ml ethanol, heated to reflux. The reaction mixture is agitated and heated under reflux for 4 hours. After the temperature returns to 20° C., the product is partitioned between 100 ml of AcOEt and 50 ml of 1M NaOH. After decanting, the organic phase is washed successively with 50 ml water and 50 ml salt water. The organic solution is dried over $Na_2SO_4$, filtered and concentrated under vacuum. A beige powder is obtained with a yield of 41%. Melting point: 146–147° C.

33.3) N-[3-(9H-carbazol-4-yloxy)propyl]-2-thiophenecarboximidamide

The experimental protocol used is the same as that described for intermediate 2.3, starting from intermediate 33.2. The expected product is isolated in the form of a free base. Pale beige solid. Melting point: 189–190° C.

Example 34

N-{4-[4-(10H-phenothiazin-2-yloxy)butyl]phenyl}-2-thiophenecarboximidamide hydroiodide: 34

The experimental protocol used is the same as that described for Example 15, starting from 4-(4-nitrophenyl)-1-butanol and 2-hydroxy-10H-phenothiazine (J. Med. Chem. (1992) 35, 716). The expected final product precipitates directly from the reaction mixture, it is isolated by filtration and washed using iPrOH. Yellow solid. Melting point: 262–270° C.

Example 35

3-[(3-{[amino(2-thienyl)methylidene]amino}-benzyl)amino]-N-(4-anilinophenyl)propanamide trihydrochloride: 35

35.1) tert-butyl 3-(4-anilinoanilino)-3-oxopropyl carbamate

The experimental protocol used is the same as that described for intermediate 2.1, starting from Boc-β-Alanine and 4-aminodiphenylamine. After rapid filtration on a silica column (eluent:Heptane/AcOEt: 1/1), the expected product is obtained with a quantitative yield.

35.2) 3-amino-N-(4-anilinophenyl)propanamide 15 g (42.2 mmol) of intermediate 35.1 is dissolved in 300 ml of AcOEt and 120 ml of an aqueous 6 N HCl solution is added. The reaction mixture is agitated vigorously, at 20° C., for 1 hour. After decantation, the aqueous phase is recovered and made basic (pH>11) by the addition of an aqueous 2 M NaOH solution. The product is then extracted using 2 times 50 ml of $CH_2Cl_2$ and the organic phase is washed with 50 ml of salt water. Afters drying over $MgSO_4$, filtration and concentration under vacuum, the residue is purified on a silica column (eluent:$CH_2Cl_2$/EtOH/$NH_4OH$ (20%): 20/5/0.5). A violet powder is obtained with a yield of 73%. Melting point: 108–110° C.

35.3) N-(4-anilinophenyl)-3-[(3-nitrobenzyl)amino]propanamide 1.40 g (5.5 mmol) of intermediate 35.2, 0.92 g (6 mmol) of 3-nitrobenzaldehyde and 3 g of 4 Å pulverulent molecular sieve which has been activated beforehand are added successively, under inert atmosphere, into a flask containing 100 ml anhydrous MeOH. The reaction mixture is agitated vigorously for 15 hours before the addition, by portions, of 0.24 g (6 mmol) of $NaBH_4$. Agitation is maintained for another 4 hours before the addition of 10 ml of water. After a quarter of an hour, the sieve is filtered out and the reaction mixture is extracted twice with 100 ml $CH_2Cl_2$. The organic phase is washed successively with 50 ml of water and 50 ml of salt water, dried over sodium sulphate, filtered and concentrated under vacuum. The residue is purified on a silica column (eluent:$CH_2Cl_2$/EtOH: 20/1). An orange oil is obtained with a yield of 94%.

35.4) 3-[(3-aminobenzyl)amino]-N-(4-anilinophenyl)propanamide

Reduction of the nitro function of intermediate 35.3 is carried out in the presence of Pd/C in ethanol, under the conditions described for intermediate 2.2. After filtration of the Pd/C and concentration under vacuum, the product is directly used in the following stage.

35.5) 3-[(3-{[amino(2-thienyl)methylidene]amino}-benzyl)amino]-N-(4-anilinophenyl)propanamide trihydrochloride 0.50 g (1.40 mmol) of intermediate 35.4 and 0.50 g (1:75 mmol) of S-methyl-2-thiophene thiocarboximide hydroiodide are dissolved in 15 ml isopropanol and 15 ml DMF in a 50 ml flask, in the presence of 0.11 ml (1.40 mmol) of pyridine. The reaction mixture is agitated for 20 hours at 23° C. After evaporation of the solvent under vacuum, the residue is taken up in 100 ml of a mixture of NaOH 1N and ethyl acetate (1/1). After decantation, the organic phase is washed with 50 ml of water followed by 50 ml of salt water. The organic solution is dried over magnesium sulphate, filtered, concentrated under vacuum and the residue is purified on a silica gel column (eluent:$CH_2Cl_2$/EtOH/$NH_4OH$ (20%): 20/5/0.5). The pure fractions are collected and concentrated under vacuum. The compound is then dissolved in methanol and salified by the addition of a 1N HCl solution in ethyl ether (10 ml). After agitation for one hour at 20° C., the reaction mixture is concentrated under vacuum to produce a pale yellow powder. Melting point: 184–186° C.

Example 36

N'-(4-{2-[(10H-phenothiazin-3-ylmethyl)amino]ethyl}phenyl)-2-thiophenecarboximidamide: 36

The experimental protocol used is the same as that described for intermediates 35.3, 35.4 and 35.5, starting from 10H-phénothiazine-3-carbaldehyde (*J. Chem. Soc.* (1951), 1834; *Bull. Soc. Chim. Fr.* (1969), 1769) and 4-nitrophenethylamine. Beige foam. MS: MH+: 457.1.

Example 37

N-(4-{[amino(2-thienyl)methylidene]amino}phenethyl)-2-methoxy-10H-phenothiazine-1-carboxamide hydrochloride: 37

The experimental protocol used is the same as that described for Example 2, starting from 2-methoxy-10H-phenothiazine-1-carboxylic acid (*J. Med. Chem.* (1992) 35(4), 716–724) and 4-nitrophenethylamine. Pale yellow solid. Melting point>200° C. (decomposition).

Example 38

N'-[4-(2-{[(2-methoxy-10H-phenothiazin-1-yl)methyl]amino}ethyl)phenyl]-2-thiophenecarboximidamide: 38

38.1) 2-methoxy-10H-phenothiazine-1-carbaldehyde 4.6 g (20 mmol) of 2-methoxy-10H-phenothiazine are dissolved, under an argon atmosphere, in a three-necked flask, containing 140 ml anhydrous ethyl ether. 20 ml (50 mmol) of a solution of nBuLi (2.5 M) in hexane is then added dropwise, at 20° C. The reaction mixture is agitated for 3 hours at 20° C. before the dropwise addition of 6.2 ml (80 mmol) of anhydrous DMF. Agitation is maintained for another 15 hours at 20° C. The whole is then poured into 150 ml ice-cooled water and the product is extracted twice using 200 ml of ethyl acetate. The organic solution is washed with 100 ml of salt water, dried over $MgSO_4$, filtered and concentrated under vacuum. The evaporation residue is taken up in diisopropyl ether, filtered and dried to produce a red solid with a yield of 30%. Melting point: 155–160° C.

38.2) N'-[4-(2-{[(2-methoxy-10H-phenothiazin-1-yl)methyl]amino}ethyl)phenyl]-2-thiophenecarboximidamide The experimental protocol used is the same as that described for Example 36, starting from intermediate 38.1 and 4-nitrophenethylamine. Grey solid. MS: MH+: 487.2.

Example 39

N'-{4-[(10H-phenothiazin-2-yloxy)methyl]phenyl}-2-thiophenecarboximidamide: 39

39.1) 2-[(4-nitrobenzyl)oxy]-10H-phenothiazine 1.08 g (5 mmol) of 2-hydroxy-10H-phenothiazine (*J. Med. Chem.* (1992) 35, 716) is dissolved, under argon atmosphere, in 20 ml anhydrous THF in a flask. The solution is then cooled down to 0° C. and 0.22 g (5.5 mmol) of NaH (60%) is added by portions. After agitation for 15 minutes, 1.2 g (5.5 mmol) of 4-nitrobenzyl bromide is added by portions and the reaction mixture is agitated for 15 hours at 20° C. before being poured into 50 ml of ice-cooled water. The product is extracted twice with 25 ml $CH_2Cl_2$ and the organic solution is washed successively with 25 ml of water and 25 ml of salt water. After drying over $MgSO_4$, filtration and concentration under vacuum, the evaporation residue is purified on a silica column (eluent:$CH_2Cl_2$/EtOH: 99/1 to 98/2). After concentration of the purest fractions, a maroon solid is obtained, which is recrystallized using isopropyl acetate. A maroon solid is finally obtained with a yield of 37%.

39.2) 4-[(10H-phenothiazin-2-yloxy)methyl]aniline 1.02 g (4.52 mmol) of $SnCl_2.2H_2O$ and 0.29 g (4.52 mmol) of Zn are added successively to a solution of 0.65 g (1.86 mmol) of intermediate 39.1 in a mixture of 9.3 ml of acetic acid and 1.2 ml of HCl (12 N). The whole is agitated for 18 hours at 20° C. The reaction mixture is then made basic by the addition of a 30% aqueous NaOH solution. The product is then extracted twice using 50 ml of $CH_2Cl_2$. The organic solution is washed with 50 ml of salt water, dried over $MgSO_4$, filtered and concentrated under vacuum. The residue is purified on a silica column (eluent:Heptane/AcOEt: 1/1). A pale yellow solid is obtained with a yield of 20%. Melting point: >175° C. (decomposition).

39.3) N'-{4-[(10H-phenothiazin-2-yloxy)methyl]phenyl}-2-thiophenecarboximidamide The experimental protocol used is the same as that described for intermediate 2.3, starting from intermediate 39.2. Salmon-pink solid. Melting point: 105–116° C.

Pharmacological Study of the Products of the Invention

Study of the Effects on Neuronal Constitutive NO Synthase of a Rat's Cerebellum

The inhibitory activity of the products of the invention is determined by measuring their effects on the conversion by NO synthase of [$^3$H]L-arginine into [$^3$H]L-citrulline according to the modified method of Bredt and Snyder (*Proc. Natl. Acad. Sci. USA*, (1990) 87: 682–685). The cerebellums of Sprague-Dawley rats (300 g—Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 µl of incubation buffer containing 100 mM of HEPES (pH 7.4), 2 mM of EDTA, 2.5 mM of $CaCl_2$, 2 mM of dithiotreitol, 2 mM of reduced NADPH and 10 µg/ml of calmodulin are distributed. 25 µl of a solution containing 100 nM of [$^3$H]L-arginine (Specific activity: 56.4 Ci/mmol, Amersham) and 40 µM of non-radioactive L-arginine is added. The reaction is initiated by adding 50 µl of homogenate, the final volume being 200 µl (the missing 25 µl are either water or the tested product). After 15 min, the reaction is stopped with 2 ml of stopping buffer (20 mM of HEPES, pH 5.5, 2 mM of EDTA). After passing the samples through a 1 ml column of DOWEX resin, the radioactivity is quantified by a liquid scintillation spectrometer. The compounds of examples 3 to 5, 7, 9 to 12, 15, 16, 18, 19, 21, 22, 26, 27, 30, 31 and 35 to 37 described above show an $IC_{50}$ lower than 3.5 µM.

Study of the Effects on Lipidic Peroxidation of the Cerebral Cortex of a Rat

The inhibitory activity of the products of the invention is determined by measuring their effects on the degree of lipidic peroxidation, determined by the concentration of malondialdehyde (MDA). The MDA produced by peroxidation of unsaturated fatty acids is a good indication of lipidic peroxidation (H Esterbauer and K H Cheeseman, *Meth. Enzymol.* (1990) 186: 407–421), Male Sprague Dawley rats weighing 200 to 250 g (Charles River) were sacrificed by decapitation. The cerebral cortex is removed, then homogenized using a Thomas potter in a 20 mM Tris-HCl buffer, pH=7.4. The homogenate was centrifuged twice at 50000 g for 10 minutes at 4° C. The pellet is stored at −80° C. On the day of the experiment, the pellet is replaced in suspension at a concentration of 1 g/15 ml and centrifuged at 515 g for 10 minutes at 4° C. The supernatant is used immediately to determine the lipidic peroxidation. The homogenate of rat's cerebral cortex (500 µl) is incubated at 37° C. for 15 minutes in the presence of the compounds to be tested or of solvent (10 µl). The lipidic peroxidation reaction is initiated by adding 50 µl of $FeCl_2$ at 1 mM, EDTA at 1 mM and ascorbic acid at 4 mM.

After incubation for 30 minutes at 37° C., the reaction is stopped by adding 50 µl of a solution of hydroxylated di tertio butyl toluene (BHT, 0.2%). The MDA is quantified using a colorimetric test, by reacting a chromogenic reagent (R), N-methyl-2-phenylindol (650 µl) with 200 µl of the homogenate for 1 hour at 45° C. The condensation of an MDA molecule with two molecules of reagent R produce a stable chromophore the maximum absorbence wavelength of which is equal to 586 nm. (Caldwell et al. *European J. Pharmacol.* (1995) 285, 203–206). The compounds of Examples 1 to 9, 12 to 19, 21 to 23, 30 and 35 to 37 described above show an $IC_{50}$ lower than 30 µM.

The invention claimed is:

1. A compound of the formula

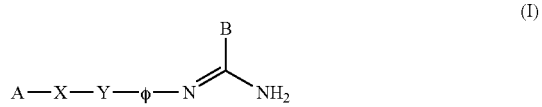

(I)

wherein

Φ is phenylene with 1 to 2 substituents selected from the group consisting of hydrogen, halogen, —OH, and alkyl or alkoxy of 1 to 6 carbon atoms;

A is

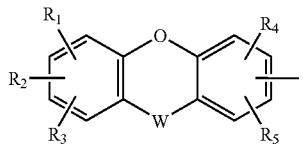

W is a bond;

R$_1$, R$_2$, R$_3$, R$_4$, R$_5$ are individually selected from the group consisting of hydrogen, halogen, —OH, alkyl or alkoxy of 1 to 6 carbon atoms, cyano, nitro and —NR$_6$R$_7$;

R$_6$ and R$_7$ are individually selected from the group consisting of hydrogen, —OH, alkyl or alkoxy of 1 to 6 carbon atoms, and —COR$_8$, R$_8$ is selected from the group consisting of hydrogen, —OH, alkyl or alkoxy of 1 to 6 carbon atoms, and —NR$_9$R$_{10}$, R$_9$ and R$_{10}$ are individually selected from the group consisting of hydrogen, —OH or alkyl of 1 to 6 carbon atoms, B is selected from the group consisting of —CH$_2$—NO$_2$; alkyl of 1 to 6 carbon atoms; —NR$_{13}$R$_{14}$; and unsubstituted or substituted carbocyclic aryl or heterocyclic aryl carbocyclic or heterocyclic aryl of 5 to 6 ring members containing 1 to 4 heteroatoms selected from the group consisting of oxygen, sulphur and nitrogen, the aryl substituents being selected from the group consisting of alkyl alkenyl and alkoxy of up to 6 carbon atoms, R$_{13}$ and R$_{14}$ are individually selected from the group consisting hydrogen, alkyl of 1 to 6 carbon atoms, cyano, nitro radical, or together with the nitrogen form a non aromatic heterocycle of 5 to 6 ring members, selected from the group consisting of —CH$_2$—, —NH—, —O— or —S—;

X is selected from the group consisting of a bond, —(CH$_2$)$_k$—NR$_{16}$—, —O—, —S—, —CO—, —NR$_{16}$—CO—, —CO—NR$_{16}$—, —O—CO—, —CO—O—, —NR$_{16}$—CO—O—, —NR$_{16}$—CO—NR$_{17}$—, k representing 0 or 1;

Y is selected from the group consisting of a bond, —(CH$_2$)$_m$—, —(CH$_2$)$_m$—O—(CH$_2$)$_n$—, —(CH$_2$)$_m$—S—(CH$_2$)$_n$—, —(CH$_2$)$_m$—NR$_{18}$—(CH$_2$)$_n$—, —(CH$_2$)$_m$—NR$_{18}$—CO—(CH$_2$)$_n$—, —(CH$_2$)$_m$—CO—NR$_{18}$—(CH$_2$)$_n$—, —(CH$_2$)$_m$-Q-(CH$_2$)$_n$—, Q is selected from the group consisting of piperazine, homopiperazine, 2-methylpiperazine, 2,5-dimethylpiperazine, 4-oxypiperidine or 4-aminopiperidine radicals, m and n are individually integers from 0 to 6;

R$_{16}$, R$_{17}$ and R$_{18}$ are individually hydrogen or akyl of 1 to 6 carbon atoms;

and a pharmaceutically acceptable salt thereof.

2. The compound of claim 1 wherein A is

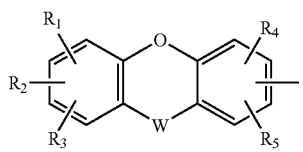

R$_1$, R$_2$, R$_3$, R$_4$, R$_5$ are individually selected from the group consisting of hydrogen, —OH and alkyl and alkoxy of 1 to 6 carbon atoms, R$_{11}$ is hydrogen or alkyl of 1 to 6 carbon atoms;

B is a substituted or unsubstituted carbocyclic aryl or heterocyclic aryl of 5 to 6 ring members containing 1 to 4 heteroatoms selected from the group consisting of oxygen, sulphur and nitrogen, the aryl substituents being selected from the group consisting of alkyl, alkenyl and alkoxy of up to 6 carbon atoms;

W is a bond

X is selected from the group consisting of a bond, —(CH$_2$)$_k$—NR$_{16}$—, —O—, —S—, —CO—, —NR$_{16}$—CO—, —CO—NR$_{16}$—, —O—CO—, —CO—O—, —NR$_{16}$—CO—O—, —NR$_{16}$—CO—NR$_{17}$—;

k representing 0 or 1;

Y is selected from the group consisting of a bond, —(CH$_2$)$_m$—, —(CH$_2$)$_m$—O—(CH$_2$)$_n$—, —(CH$_2$)$_m$—S—(CH$_2$)$_n$—, —(CH$_2$)$_m$—NR$_{18}$—(CH$_2$)$_n$—, —(CH$_2$)$_m$ NR$_{18}$—CO—(CH$_2$)$_n$—, —(CH$_2$)$_m$—CO—NR$_{18}$—(CH$_2$)$_n$—, —(CH$_2$)$_m$-Q-(CH$_2$)$_n$—;

Q is selected from the group consisting of piperazine, homopiperazine, 2-methylpiperazine, 2,5-dimethylpiperazine, 4-oxypiperidine or 4-aminopiperidine, m and n are integers from 0 to 6.

3. The compound of claim 1 wherein B as heterocyclic aryl is selected from the group consisting of thiophene, furan, pyrrole and thiazole.

4. The compound of claim 1 wherein A is

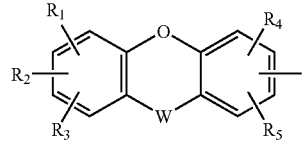

R$_1$, R$_2$, R$_3$, R$_4$ and R$_5$ are individually selected from the group consisting of hydrogen, —OH and alkyl and alkoxy of 1 to 6 carbon atoms, R$_{11}$ is hydrogen or methyl;

B is selected from the group consisting of unsusbstituted or substituted phenyl, thiophene, furan, pyrrole and thiazole, the substituents being at least one member of the group consisting of alkyl alkenyl and alkoxy of 1 to 6 carbon atoms;

W is a bond;

X is selected from the group consisting of a bond, —(CH$_2$)$_k$—NR$_{16}$—, —O—, —S—, —CO—, —NR$_{16}$—CO—, —CO—NR$_{16}$—, —O—CO—, —CO—O—, —NR$_{16}$—CO—O—, —NR$_{16}$CO—NR$_{17}$—, k representing 0 or 1;

Y is selected from the group consisting of a bond, —(CH$_2$)$_m$—, —CH$_2$)$_m$—O—(CH$_2$)$_n$—, —(CH$_2$)$_m$—S—(CH$_2$)$_n$—, —(CH$_2$)$_m$—NR$_{18}$—(CH$_2$)$_n$—, —(CH$_2$)$_m$ NR$_{18}$—CO—(CH$_2$)$_n$—, —(CH$_2$)$_m$—CO—NR$_{18}$—(CH$_2$)$_n$—, —(CH$_2$)$_m$-Q-(CH$_2$)$_n$—, Q is selected from the group consisting of piperazine, homopiperazine, 2-methylpiperazine, 2,5-dimethylpiperazine, 4oxypiperidine or 4-aminopiperidine, m and n being integers comprised from 0 to 6.

5. A compound of claim 1 which is 4-(4-{[amino(2-thienyl)methylidene]amino}phenyl)-N-(4-phenoxyphenyl)butanamide or N-(4-{[amino(2-thienyl)methylidene]amino}phenethyl)-4-(4-hydroxyphénoxy)benzamide.

6. A compound of claim 5 in the form of its hydrochloride salt.

7. A composition for inhibiting NO synthase and/or lipidic peroxidation comprising an effective amount of a compound of claim 1 and an inert pharmaceutical carrier.

* * * * *